(12) United States Patent
Greenhalgh et al.

(10) Patent No.: US 9,770,339 B2
(45) Date of Patent: Sep. 26, 2017

(54) EXPANDABLE SUPPORT DEVICE AND METHOD OF USE

(75) Inventors: E. Skott Greenhalgh, Wyndmoor, PA (US); John-Paul Romano, Chalfont, PA (US); Michael P. Igoe, Perkasie, PA (US); Robert A. Kiefer, Quakertown, PA (US)

(73) Assignee: Stout Medical Group, L.P., Quakertown, PA (US)

( * ) Notice: Subject to any disclaimer, the term of this patent is extended or adjusted under 35 U.S.C. 154(b) by 306 days.

(21) Appl. No.: 12/014,006

(22) Filed: Jan. 14, 2008

(65) Prior Publication Data
US 2008/0183204 A1  Jul. 31, 2008

Related U.S. Application Data

(63) Continuation of application No. PCT/US2006/027601, filed on Jul. 14, 2006.
(Continued)

(51) Int. Cl.
*A61M 29/00* (2006.01)
*A61F 2/44* (2006.01)
(Continued)

(52) U.S. Cl.
CPC ........ *A61F 2/4455* (2013.01); *A61B 17/8858* (2013.01); *A61F 2/4611* (2013.01);
(Continued)

(58) Field of Classification Search
CPC .. A61F 2/89; A61F 2/915; A61F 2002/91533; A61F 2002/91541;
(Continued)

(56) References Cited

U.S. PATENT DOCUMENTS

| 646,119 A | 3/1900 | Clamer et al. |
| 4,204,531 A | 5/1980 | Aginsky |

(Continued)

FOREIGN PATENT DOCUMENTS

| DE | 19710392 | 7/1999 |
| EP | 0734702 | 10/1996 |

(Continued)

OTHER PUBLICATIONS

Database WPI, Week 198004, Thomson Scientific, London, GB; AN 1980-A8866C, XP002690114, -& SU 662 082 A1 (Tartus Univ) May 15, 1979 (May 15, 1979), abstract, figures 1,2.
(Continued)

*Primary Examiner* — Paul Prebilic
(74) *Attorney, Agent, or Firm* — Levin Bagade Han LLP

(57) ABSTRACT

An expandable support device for tissue repair is disclosed. The device can be used to repair hard or soft tissue, such as bone or vertebral discs. The device can have multiple flat sides that remain flat during expansion. A method of repairing tissue is also disclosed. Devices and methods for adjusting (e.g., removing, repositioning, resizing) deployed orthopedic expandable support devices are also disclosed. The expandable support devices can be engaged by an engagement device. The engagement device can longitudinally expand the expandable support device. The expandable support device can be longitudinally expanded until the expandable support device is substantially in a pre-deployed configuration. The expandable support device can be then be physically translated and/or rotated.

22 Claims, 22 Drawing Sheets

Related U.S. Application Data

(60) Provisional application No. 60/699,576, filed on Jul. 14, 2005, provisional application No. 60/752,183, filed on Dec. 19, 2005.

(51) Int. Cl.
  A61B 17/88 (2006.01)
  A61F 2/46 (2006.01)
  A61B 17/70 (2006.01)
  A61B 17/00 (2006.01)
  A61F 2/30 (2006.01)

(52) U.S. Cl.
  CPC . *A61B 17/7098* (2013.01); *A61B 2017/00004* (2013.01); *A61F 2/442* (2013.01); *A61F 2002/30092* (2013.01); *A61F 2002/3097* (2013.01); *A61F 2002/30135* (2013.01); *A61F 2002/30166* (2013.01); *A61F 2002/30176* (2013.01); *A61F 2002/30177* (2013.01); *A61F 2002/30579* (2013.01); *A61F 2002/30677* (2013.01); *A61F 2002/30787* (2013.01); *A61F 2002/30978* (2013.01); *A61F 2002/4475* (2013.01); *A61F 2002/4627* (2013.01); *A61F 2002/4629* (2013.01); *A61F 2210/0014* (2013.01); *A61F 2230/0004* (2013.01); *A61F 2230/0028* (2013.01); *A61F 2230/0054* (2013.01); *A61F 2230/0056* (2013.01); *A61F 2310/00017* (2013.01); *A61F 2310/00023* (2013.01); *A61F 2310/00029* (2013.01); *A61F 2310/00137* (2013.01); *A61F 2310/00952* (2013.01)

(58) Field of Classification Search
  CPC .......... A61F 2002/91583; A61F 2/4611; A61F 2/4455; A61F 2/447; A61F 2002/4475
  See application file for complete search history.

(56) References Cited

U.S. PATENT DOCUMENTS

| | | | |
|---|---|---|---|
| 4,541,423 A | 9/1985 | Barber | |
| 4,569,338 A | 2/1986 | Edwards | |
| 4,636,217 A | 1/1987 | Ogilvie et al. | |
| 4,653,489 A | 3/1987 | Tronzo | |
| 4,716,839 A | 1/1988 | Catena | |
| 4,716,893 A | 1/1988 | Fischer et al. | |
| 4,725,264 A * | 2/1988 | Glassman | 604/102.03 |
| 4,733,665 A | 3/1988 | Palmaz | |
| 4,759,769 A | 7/1988 | Hedman et al. | |
| 4,763,644 A | 8/1988 | Webb | |
| 4,863,476 A | 9/1989 | Shepperd | |
| 4,886,062 A | 12/1989 | Wiktor | |
| 4,911,718 A | 3/1990 | Lee et al. | |
| 4,932,975 A | 6/1990 | Main et al. | |
| 4,941,466 A | 7/1990 | Romano | |
| 4,969,888 A | 11/1990 | Scholten et al. | |
| 5,007,909 A | 4/1991 | Rogozinski | |
| 5,015,247 A | 5/1991 | Michelson | |
| 5,026,373 A | 6/1991 | Ray et al. | |
| 5,059,193 A * | 10/1991 | Kuslich | 606/247 |
| 5,108,404 A | 4/1992 | Scholten et al. | |
| 5,123,926 A | 6/1992 | Pisharodi | |
| 5,139,480 A | 8/1992 | Hickle et al. | |
| 5,171,278 A | 12/1992 | Pisharodi | |
| 5,217,483 A | 6/1993 | Tower | |
| 5,258,031 A | 11/1993 | Salib et al. | |
| 5,273,533 A | 12/1993 | Bonaldo | |
| 5,306,278 A | 4/1994 | Dahl et al. | |
| 5,324,295 A | 6/1994 | Shapiro, III | |
| 5,342,348 A | 8/1994 | Kaplan | |
| 5,345,927 A | 9/1994 | Bonutti | |
| 5,390,683 A * | 2/1995 | Pisharodi | 128/898 |
| 5,390,898 A | 2/1995 | Smedley et al. | |
| 5,397,364 A | 3/1995 | Kozak et al. | |
| 5,425,773 A | 6/1995 | Boyd et al. | |
| 5,454,365 A * | 10/1995 | Bonutti | 600/204 |
| 5,458,643 A | 10/1995 | Oka et al. | |
| 5,480,442 A | 1/1996 | Bertagnoli | |
| 5,484,384 A | 1/1996 | Fearnot | |
| 5,496,365 A * | 3/1996 | Sgro | 623/1.2 |
| 5,522,899 A | 6/1996 | Michelson | |
| 5,534,002 A | 7/1996 | Brumfield et al. | |
| 5,540,690 A | 7/1996 | Miller et al. | |
| 5,549,679 A | 8/1996 | Kuslich | |
| 5,554,191 A | 9/1996 | Lahille et al. | |
| 5,556,413 A | 9/1996 | Lam | |
| 5,562,736 A | 10/1996 | Ray et al. | |
| 5,562,738 A | 10/1996 | Boyd et al. | |
| 5,571,189 A | 11/1996 | Kuslich | |
| 5,571,192 A | 11/1996 | Schonhoffer | |
| 5,584,831 A | 12/1996 | McKay | |
| 5,591,197 A | 1/1997 | Orth et al. | |
| 5,593,409 A | 1/1997 | Michelson | |
| 5,609,356 A | 3/1997 | Mossi | |
| 5,609,635 A | 3/1997 | Michelson | |
| 5,643,264 A | 7/1997 | Sherman et al. | |
| 5,643,312 A * | 7/1997 | Fischell et al. | 623/1.15 |
| 5,645,560 A | 7/1997 | Crocker et al. | |
| 5,653,763 A | 8/1997 | Errico et al. | |
| 5,658,335 A | 8/1997 | Allen | |
| 5,665,122 A | 9/1997 | Kambin | |
| 5,669,909 A | 9/1997 | Zdeblick et al. | |
| 5,674,295 A | 10/1997 | Ray et al. | |
| 5,683,394 A | 11/1997 | Rinner | |
| 5,693,100 A | 12/1997 | Pisharodi | |
| 5,702,449 A | 12/1997 | McKay | |
| 5,702,453 A | 12/1997 | Rabbe et al. | |
| 5,741,253 A | 4/1998 | Michelson | |
| 5,749,916 A | 5/1998 | Richelsoph | |
| 5,772,661 A | 6/1998 | Michelson | |
| 5,776,181 A * | 7/1998 | Lee et al. | 623/1.15 |
| 5,776,197 A | 7/1998 | Rabbe et al. | |
| 5,776,198 A | 7/1998 | Rabbe et al. | |
| 5,776,199 A | 7/1998 | Michelson | |
| 5,782,832 A | 7/1998 | Larsen et al. | |
| 5,782,903 A | 7/1998 | Wiktor | |
| 5,785,710 A | 7/1998 | Michelson | |
| 5,800,520 A | 9/1998 | Fogarty et al. | |
| 5,824,054 A | 10/1998 | Khosravi et al. | |
| 5,824,093 A | 10/1998 | Ray et al. | |
| 5,827,289 A | 10/1998 | Reiley et al. | |
| 5,827,321 A | 10/1998 | Roubin et al. | |
| 5,853,419 A * | 12/1998 | Imran | 623/1.15 |
| 5,861,025 A * | 1/1999 | Boudghene et al. | 623/1.15 |
| 5,863,284 A | 1/1999 | Klein | |
| 5,865,848 A | 2/1999 | Baker | |
| 5,895,387 A | 4/1999 | Guerrero et al. | |
| 5,902,475 A | 5/1999 | Trozera et al. | |
| 5,916,198 A | 6/1999 | Dillow | |
| 5,972,015 A | 10/1999 | Scribner et al. | |
| 5,980,522 A | 11/1999 | Koros et al. | |
| 5,980,550 A | 11/1999 | Eder et al. | |
| 5,984,957 A | 11/1999 | Laptewicz et al. | |
| 5,993,483 A | 11/1999 | Gianotti | |
| 6,001,130 A | 12/1999 | Bryan et al. | |
| 6,019,792 A | 2/2000 | Cauthen | |
| 6,022,376 A | 2/2000 | Assell et al. | |
| 6,025,104 A | 2/2000 | Fuller et al. | |
| 6,027,527 A * | 2/2000 | Asano et al. | 623/1.15 |
| 6,036,719 A | 3/2000 | Meilus | |
| 6,039,761 A | 3/2000 | Li et al. | |
| 6,045,579 A | 4/2000 | Hochshuler et al. | |
| 6,053,916 A | 4/2000 | Moore | |
| 6,066,154 A | 5/2000 | Reiley et al. | |
| 6,077,246 A | 6/2000 | Kullas et al. | |
| 6,080,158 A | 6/2000 | Lin | |
| 6,080,193 A | 6/2000 | Hochshuler et al. | |
| 6,083,522 A | 7/2000 | Chu et al. | |
| 6,086,610 A | 7/2000 | Duerig et al. | |
| 6,090,143 A | 7/2000 | Meriwether et al. | |
| 6,102,950 A | 8/2000 | Vaccaro | |

(56) References Cited

U.S. PATENT DOCUMENTS

| | | | |
|---|---|---|---|
| 6,113,639 A | 9/2000 | Ray et al. | |
| 6,126,689 A | 10/2000 | Brett | |
| 6,127,597 A * | 10/2000 | Beyar et al. | 606/86 R |
| 6,129,763 A | 10/2000 | Chauvin et al. | |
| 6,132,465 A | 10/2000 | Ray et al. | |
| 6,140,452 A | 10/2000 | Felt et al. | |
| 6,146,417 A | 11/2000 | Ischinger | |
| 6,159,244 A | 12/2000 | Suddaby | |
| 6,159,245 A | 12/2000 | Meriwether et al. | |
| 6,168,616 B1 | 1/2001 | Brown, III | |
| 6,171,312 B1 | 1/2001 | Beaty | |
| 6,176,882 B1 | 1/2001 | Biedermann et al. | |
| 6,179,874 B1 | 1/2001 | Cauthen | |
| 6,183,506 B1 * | 2/2001 | Penn et al. | 623/1.15 |
| 6,183,517 B1 | 2/2001 | Suddaby | |
| 6,193,757 B1 | 2/2001 | Foley et al. | |
| 6,206,910 B1 * | 3/2001 | Berry et al. | 623/1.15 |
| 6,206,924 B1 | 3/2001 | Timm | |
| 6,224,595 B1 | 5/2001 | Michelson | |
| 6,224,603 B1 | 5/2001 | Marino | |
| 6,224,604 B1 | 5/2001 | Suddaby | |
| 6,224,607 B1 | 5/2001 | Michelson | |
| 6,235,043 B1 | 5/2001 | Reiley et al. | |
| 6,241,734 B1 | 6/2001 | Scribner et al. | |
| 6,245,101 B1 | 6/2001 | Drasler et al. | |
| 6,245,107 B1 | 6/2001 | Ferree | |
| 6,248,110 B1 | 6/2001 | Reiley et al. | |
| 6,280,456 B1 | 8/2001 | Scribner et al. | |
| 6,287,332 B1 | 9/2001 | Bolz et al. | |
| 6,293,967 B1 | 9/2001 | Shanley | |
| 6,302,914 B1 | 10/2001 | Michelson | |
| 6,332,895 B1 | 12/2001 | Suddaby | |
| 6,371,989 B1 | 4/2002 | Chauvin et al. | |
| 6,387,130 B1 | 5/2002 | Stone et al. | |
| 6,395,031 B1 | 5/2002 | Foley et al. | |
| 6,402,750 B1 | 6/2002 | Atkinson et al. | |
| 6,402,785 B1 | 6/2002 | Zdeblick et al. | |
| 6,409,765 B1 | 6/2002 | Bianchi et al. | |
| 6,419,704 B1 | 7/2002 | Ferree | |
| 6,419,705 B1 | 7/2002 | Erickson | |
| 6,423,083 B2 | 7/2002 | Reiley et al. | |
| 6,425,916 B1 | 7/2002 | Garrison et al. | |
| 6,425,919 B1 | 7/2002 | Lambrecht | |
| 6,428,569 B1 | 8/2002 | Brown | |
| 6,432,107 B1 | 8/2002 | Ferree | |
| 6,436,098 B1 | 8/2002 | Michelson | |
| 6,436,140 B1 | 8/2002 | Liu et al. | |
| 6,440,168 B1 | 8/2002 | Cauthen | |
| 6,447,544 B1 | 9/2002 | Michelson | |
| 6,447,546 B1 | 9/2002 | Bramlet et al. | |
| 6,447,547 B1 | 9/2002 | Michelson | |
| 6,451,025 B1 | 9/2002 | Jervis | |
| 6,454,804 B1 | 9/2002 | Ferree | |
| 6,468,301 B1 | 10/2002 | Amplatz et al. | |
| 6,468,302 B2 | 10/2002 | CoC et al. | |
| 6,478,823 B1 | 11/2002 | Michelson | |
| 6,482,235 B1 | 11/2002 | Lambrecht et al. | |
| 6,488,710 B2 | 12/2002 | Besselink | |
| 6,491,724 B1 | 12/2002 | Ferree | |
| 6,494,883 B1 | 12/2002 | Ferree | |
| 6,508,839 B1 | 1/2003 | Lambrecht et al. | |
| 6,514,255 B1 | 2/2003 | Ferree | |
| 6,520,991 B2 | 2/2003 | Huene | |
| 6,533,817 B1 | 3/2003 | Norton et al. | |
| 6,554,833 B2 | 4/2003 | Levy et al. | |
| 6,562,074 B2 | 5/2003 | Gerbec et al. | |
| 6,582,431 B1 | 6/2003 | Ray | |
| 6,582,467 B1 | 6/2003 | Teitelbaum et al. | |
| 6,585,770 B1 | 7/2003 | White et al. | |
| 6,592,589 B2 | 7/2003 | Hajianpour | |
| 6,592,625 B2 | 7/2003 | Cauthen | |
| 6,595,998 B2 | 7/2003 | Johnson et al. | |
| 6,602,291 B1 | 8/2003 | Ray et al. | |
| 6,607,530 B1 | 8/2003 | Carl et al. | |
| 6,607,544 B1 | 8/2003 | Boucher et al. | |
| 6,613,054 B2 | 9/2003 | Scribner et al. | |
| 6,623,505 B2 | 9/2003 | Scribner et al. | |
| 6,641,587 B2 | 11/2003 | Scribner et al. | |
| 6,641,614 B1 | 11/2003 | Wagner et al. | |
| 6,645,213 B2 | 11/2003 | Sand et al. | |
| 6,645,247 B2 | 11/2003 | Ferree | |
| 6,648,917 B2 | 11/2003 | Gerbec et al. | |
| 6,648,918 B2 | 11/2003 | Ferree | |
| 6,648,920 B2 | 11/2003 | Ferree | |
| 6,652,584 B2 | 11/2003 | Michelson | |
| 6,656,178 B1 | 12/2003 | Veldhuizen et al. | |
| 6,663,647 B2 | 12/2003 | Reiley et al. | |
| 6,666,891 B2 | 12/2003 | Boehm, Jr. et al. | |
| 6,676,665 B2 | 1/2004 | Foley et al. | |
| 6,679,915 B1 | 1/2004 | Cauthen | |
| 6,685,695 B2 | 2/2004 | Ferree | |
| 6,695,760 B1 | 2/2004 | Winkler et al. | |
| 6,706,068 B2 | 3/2004 | Ferree | |
| 6,706,070 B1 | 3/2004 | Wagner et al. | |
| 6,709,458 B2 | 3/2004 | Michelson | |
| 6,712,853 B2 | 3/2004 | Kuslich | |
| 6,716,216 B1 | 4/2004 | Boucher et al. | |
| 6,716,247 B2 | 4/2004 | Michelson | |
| 6,719,773 B1 | 4/2004 | Boucher et al. | |
| 6,723,126 B1 | 4/2004 | Berry | |
| 6,726,691 B2 | 4/2004 | Osorio et al. | |
| 6,733,535 B2 | 5/2004 | Michelson | |
| 6,740,090 B1 | 5/2004 | Cragg et al. | |
| 6,743,255 B2 | 6/2004 | Ferree | |
| 6,746,451 B2 | 6/2004 | Middleton et al. | |
| 6,758,863 B2 * | 7/2004 | Estes et al. | 623/17.16 |
| 6,793,656 B1 | 9/2004 | Mathews | |
| 6,793,679 B2 | 9/2004 | Michelson | |
| 6,808,537 B2 | 10/2004 | Michelson | |
| 6,814,756 B1 | 11/2004 | Michelson | |
| 6,830,589 B2 | 12/2004 | Erickson | |
| 6,852,115 B2 | 2/2005 | Kinnett | |
| 6,852,123 B2 | 2/2005 | Brown | |
| 6,852,129 B2 | 2/2005 | Gerbec et al. | |
| 6,863,673 B2 | 3/2005 | Gerbec et al. | |
| 6,893,464 B2 | 5/2005 | Kiester | |
| 6,899,716 B2 | 5/2005 | Cragg | |
| 6,899,719 B2 | 5/2005 | Reiley et al. | |
| 6,921,264 B2 | 6/2005 | Mayer et al. | |
| 6,923,813 B2 | 8/2005 | Phillips et al. | |
| 6,923,830 B2 | 8/2005 | Michelson | |
| 6,936,065 B2 | 8/2005 | Khan et al. | |
| 6,936,070 B1 | 8/2005 | Muhanna | |
| 6,948,223 B2 | 9/2005 | Shortt | |
| 6,953,477 B2 | 10/2005 | Berry | |
| 6,955,691 B2 | 10/2005 | Chae et al. | |
| 6,960,215 B2 | 11/2005 | Olson et al. | |
| 6,962,606 B2 | 11/2005 | Michelson | |
| 6,981,981 B2 | 1/2006 | Reiley et al. | |
| 6,988,710 B2 | 1/2006 | Igarashi | |
| 7,008,453 B1 | 3/2006 | Michelson | |
| 7,018,415 B1 | 3/2006 | McKay | |
| 7,018,416 B2 | 3/2006 | Hanson et al. | |
| 7,056,321 B2 | 6/2006 | Pagliuca et al. | |
| 7,060,073 B2 | 6/2006 | Frey et al. | |
| 7,066,961 B2 | 6/2006 | Michelson | |
| 7,077,864 B2 | 7/2006 | Byrd et al. | |
| 7,087,055 B2 | 8/2006 | Lim et al. | |
| 7,094,257 B2 | 8/2006 | Mujwid et al. | |
| 7,097,648 B1 | 8/2006 | Globerman et al. | |
| 7,112,206 B2 | 9/2006 | Michelson | |
| 7,118,598 B2 | 10/2006 | Michelson | |
| 7,135,043 B2 | 11/2006 | Nakahara et al. | |
| 7,166,110 B2 | 1/2007 | Yundt | |
| 7,201,751 B2 | 4/2007 | Zucherman et al. | |
| 7,201,775 B2 | 4/2007 | Gorensek et al. | |
| 7,204,853 B2 | 4/2007 | Gordon et al. | |
| 7,211,112 B2 | 5/2007 | Baynham et | |
| 7,212,480 B2 | 5/2007 | Shoji et al. | |
| 7,223,292 B2 | 5/2007 | Messerli et al. | |
| 7,226,475 B2 | 6/2007 | Lenz et al. | |
| 7,226,481 B2 | 6/2007 | Kuslich | |
| 7,226,483 B2 | 6/2007 | Gerber et al. | |
| 7,238,186 B2 | 7/2007 | Zdeblick et al. | |

(56) References Cited

U.S. PATENT DOCUMENTS

| | | |
|---|---|---|
| 7,241,276 B2 | 7/2007 | Argentine et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,431,735 B2 | 10/2008 | Liu et al. |
| 7,452,371 B2 | 11/2008 | Pavcnik et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,625,395 B2 | 12/2009 | Mückter |
| 7,722,674 B1 | 5/2010 | Grotz |
| 7,763,028 B2 * | 7/2010 | Lim et al. ............... 606/90 |
| 7,828,849 B2 | 11/2010 | Lim |
| 7,837,734 B2 | 11/2010 | Zucherman et al. |
| 7,867,233 B2 | 1/2011 | Shaolian et al. |
| 7,875,035 B2 | 1/2011 | Boucher et al. |
| 7,879,082 B2 | 2/2011 | Brown |
| 8,007,498 B2 | 8/2011 | Mische |
| 8,034,110 B2 | 10/2011 | Garner et al. |
| 8,105,382 B2 | 1/2012 | Olmos et al. |
| 8,142,507 B2 | 3/2012 | McGuckin |
| 8,551,171 B2 | 10/2013 | Johnson et al. |
| 8,591,582 B2 | 11/2013 | Anderson et al. |
| 8,709,042 B2 | 4/2014 | Greenhalgh et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0038767 A1 | 4/2002 | Trozera |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 * | 10/2002 | Michelson ............... 623/17.16 |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0171813 A1 | 9/2003 | Kiester |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | McGuckin |
| 2003/0199981 A1 | 10/2003 | Ferree |
| 2003/0204189 A1 | 10/2003 | Cragg |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0233188 A1 | 12/2003 | Jones |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | McKay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087947 A1 | 5/2004 | Lim et al. |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0097927 A1 | 5/2004 | Yeung et al. |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |

(56) References Cited

U.S. PATENT DOCUMENTS

| | | |
|---|---|---|
| 2004/0153146 A1 | 8/2004 | Lashinski et al. |
| 2004/0167625 A1 | 8/2004 | Beyar et al. |
| 2004/0172019 A1 | 9/2004 | Ferree |
| 2005/0010292 A1 | 1/2005 | Carrasco |
| 2005/0015152 A1 | 1/2005 | Sweeney |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0228472 A1 | 10/2005 | Case et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261695 A1 | 11/2005 | Cragg et al. |
| 2005/0261768 A1 | 11/2005 | Trieu |
| 2005/0261781 A1 | 11/2005 | Sennett et al. |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0022180 A1 | 2/2006 | Selness |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0079898 A1 | 4/2006 | Ainsworth et al. |
| 2006/0085069 A1 * | 4/2006 | Kim ................. 623/17.11 |
| 2006/0085070 A1 | 4/2006 | Kim |
| 2006/0089715 A1 | 4/2006 | Truckai et al. |
| 2006/0095123 A1 | 5/2006 | Flanagan |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0142859 A1 | 6/2006 | McLuen |
| 2006/0149239 A1 | 7/2006 | Winslow et al. |
| 2006/0149349 A1 | 7/2006 | Garbe |
| 2006/0149385 A1 | 7/2006 | McKay |
| 2006/0155379 A1 | 7/2006 | Heneveld et al. |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0184248 A1 | 8/2006 | Edidin et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0241764 A1 | 10/2006 | Michelson |
| 2006/0253201 A1 | 11/2006 | McLuen |
| 2006/0264968 A1 | 11/2006 | Frey et al. |
| 2006/0265077 A1 | 11/2006 | Zwirkoski |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055377 A1 | 3/2007 | Hanson et al. |
| 2007/0067034 A1 | 3/2007 | Chirico et al. |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123986 A1 | 5/2007 | Schaller |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 * | 7/2007 | Kim et al. ................. 623/17.11 |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0233260 A1 | 10/2007 | Cragg |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0082162 A1 | 4/2008 | Boismier et al. |
| 2008/0125865 A1 | 5/2008 | Abdelgany |
| 2008/0133012 A1 | 6/2008 | McGuckin |
| 2008/0140082 A1 | 6/2008 | Erdem et al. |
| 2008/0140179 A1 | 6/2008 | Ladisa |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0188941 A1 | 8/2008 | Grotz |
| 2008/0208255 A1 | 8/2008 | Siegal |
| 2008/0221687 A1 | 9/2008 | Viker |
| 2008/0243254 A1 | 10/2008 | Butler |
| 2008/0294205 A1 | 11/2008 | Greenhalgh et al. |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0143859 A1 | 6/2009 | McClellan et al. |
| 2009/0149956 A1 | 6/2009 | Greenhalgh et al. |
| 2009/0163918 A1 | 6/2009 | Levy et al. |
| 2009/0182336 A1 | 7/2009 | Brenzel et al. |
| 2009/0198338 A1 | 8/2009 | Phan |
| 2009/0234398 A1 | 9/2009 | Chirico et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0324560 A1 | 12/2010 | Suda |
| 2011/0009869 A1 | 1/2011 | Marino et al. |
| 2011/0054621 A1 | 3/2011 | Lim |
| 2011/0106260 A1 | 5/2011 | Laurence et al. |
| 2011/0125266 A1 | 5/2011 | Rodgers et al. |
| 2011/0319898 A1 | 12/2011 | O'Neil et al. |
| 2011/0320000 A1 | 12/2011 | O'Neil et al. |

FOREIGN PATENT DOCUMENTS

| | | | |
|---|---|---|---|
| EP | 0758541 | 2/1997 | |
| FR | 2900814 | 11/2007 | |
| JP | 2000-210315 | 8/2000 | |
| JP | 2003-512887 | 4/2003 | |
| JP | 2004-531355 | 10/2004 | |
| JP | 2004-321348 | 11/2004 | |
| SU | 662082 | 5/1979 | |
| WO | WO 88/03781 | 6/1988 | |
| WO | WO 92/14423 | 9/1992 | |
| WO | WO 95/31945 | 11/1995 | |
| WO | WO 96/03092 | 2/1996 | |
| WO | WO 97/00054 | 1/1997 | |
| WO | WO 00/30523 | 6/2000 | |
| WO | WO 00/44321 | 8/2000 | |
| WO | WO 0044319 | * 8/2000 | ............... A61F 2/44 |

(56) References Cited

FOREIGN PATENT DOCUMENTS

| | | |
|---|---|---|
| WO | WO 01/32099 | 5/2001 |
| WO | WO 01/78625 | 10/2001 |
| WO | WO 01/95838 | 12/2001 |
| WO | WO 02/13700 | 2/2002 |
| WO | WO 02/32347 | 4/2002 |
| WO | WO 03/003943 | 1/2003 |
| WO | WO 03/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116761 | 11/2006 |
| WO | WO 2006/132945 | 12/2006 |
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/075411 | 7/2007 |
| WO | WO 2007/079021 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/113808 | 10/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2009/067568 | 5/2009 |
| WO | WO 2012/027490 | 3/2012 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and *Chlamydia Pneumoniae*," *Brit., J. Surgery*, 88(7):935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

Choi, G. et al., "Percutaneous Endoscopic Lumbar Discemtomy by Transiliac Approach," *Spine*, 34(12):E443-446, May 20, 2009.

Franklin, I.J. et al., "Uptake of Tetracycline by Aortic Aneurysm Wall and Its Effect on Inflammation and Proteolysis," *Brit. J. Surger*, 86(6):771-775, Jun. 1999.

\* cited by examiner

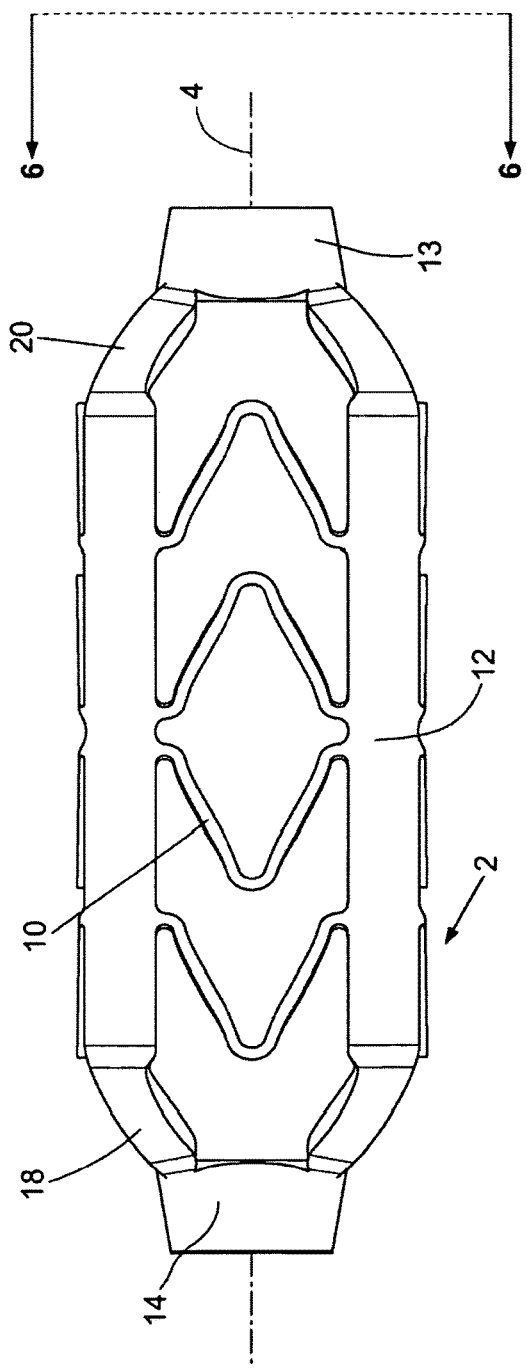
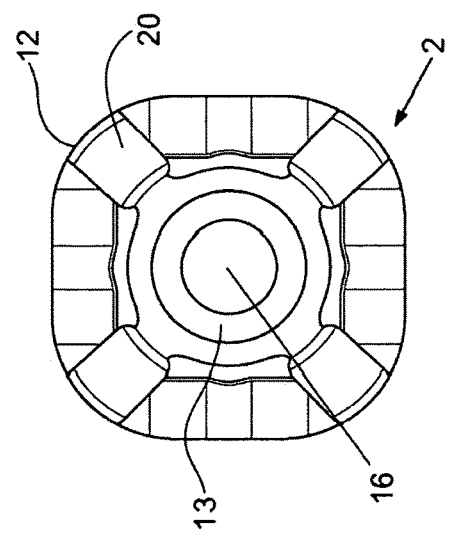
Fig. 5
Fig. 6

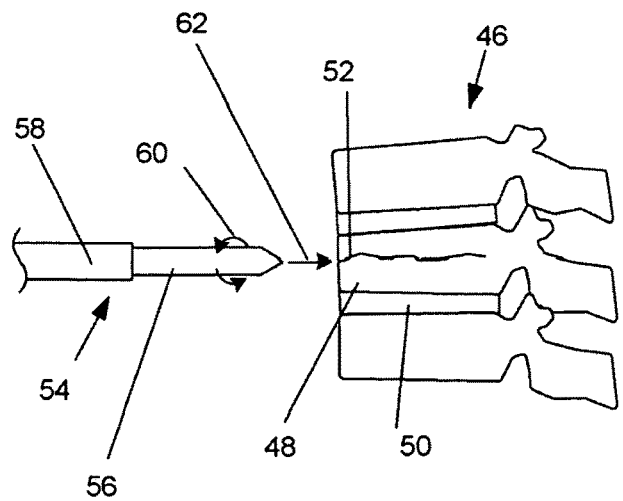
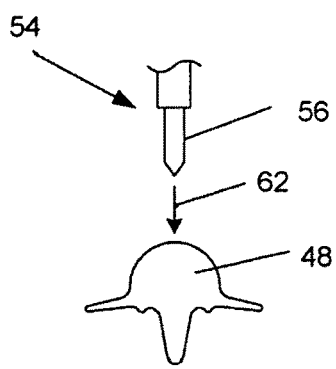
Fig. 9  Fig. 10
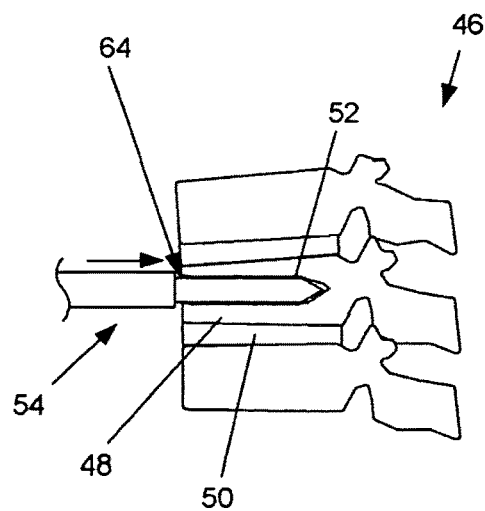
Fig. 11

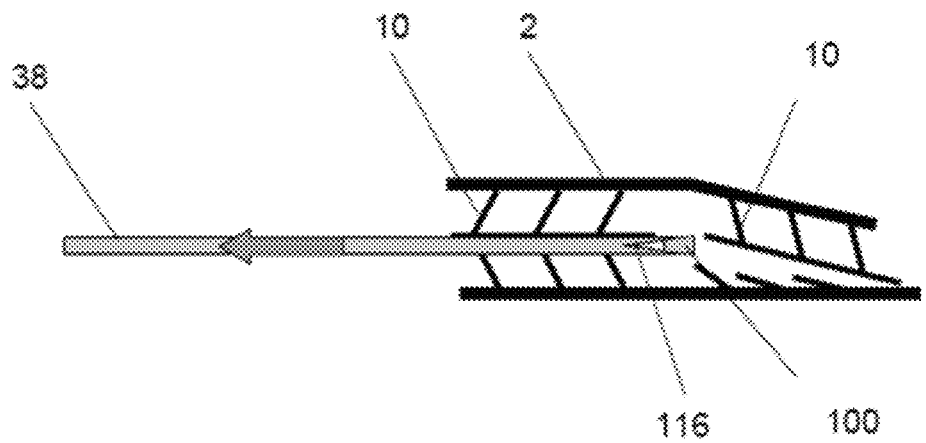
Figure 35
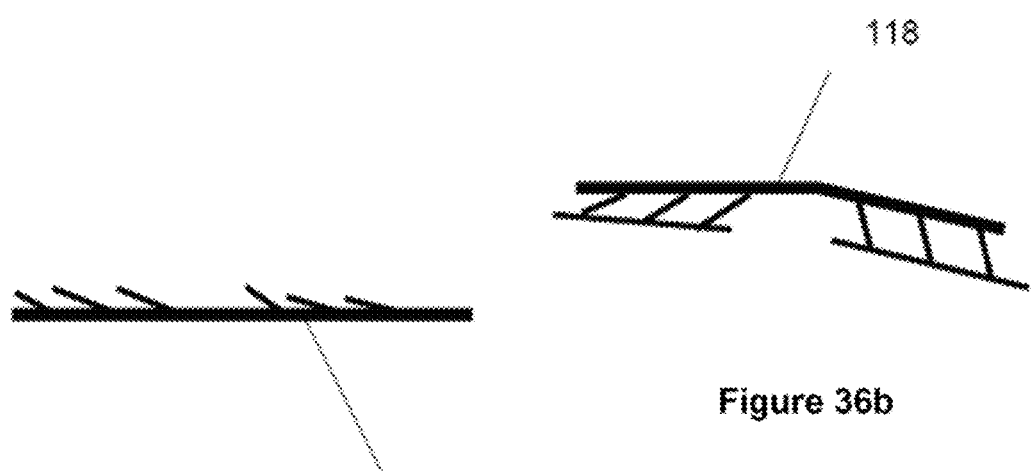
Figure 36a
Figure 36b

EXPANDABLE SUPPORT DEVICE AND METHOD OF USE

CROSS-REFERENCE TO RELATED APPLICATIONS

This application is a continuation of PCT Application No. PCT/US2006/027601, filed 14 Jul. 2006, which claims the benefit to U.S. Provisional Application Nos. 60/699,576 filed 14 Jul. 2005, and 60/752,183 filed 19 Dec. 2005, which are all herein incorporated by reference in their entireties.

BACKGROUND OF THE INVENTION

This invention relates to devices for providing support for biological tissue, for example to repair spinal compression fractures, and methods of using the same.

Vertebroplasty is an image-guided, minimally invasive, nonsurgical therapy used to strengthen a broken vertebra that has been weakened by disease, such as osteoporosis or cancer. Vertebroplasty is often used to treat compression fractures, such as those caused by osteoporosis, cancer, or stress.

Vertebroplasty is often performed on patients too elderly or frail to tolerate open spinal surgery, or with bones too weak for surgical spinal repair. Patients with vertebral damage due to a malignant tumor may sometimes benefit from vertebroplasty. The procedure can also be used in younger patients whose osteoporosis is caused by long-term steroid treatment or a metabolic-disorder.

Vertebroplasty can increase the patient's functional abilities, allow a return to the previous level of activity, and prevent further vertebral collapse. Vertebroplasty attempts to also alleviate the pain caused by a compression fracture.

Vertebroplasty is often accomplished by injecting an orthopedic cement mixture through a needle into the fractured bone. The cement mixture can leak from the bone, potentially entering a dangerous location such as the spinal canal. The cement mixture, which is naturally viscous, is difficult to inject through small diameter needles, and thus many practitioners choose to "thin out" the cement mixture to improve cement injection, which ultimately exacerbates the leakage problems. The flow of the cement liquid also naturally follows the path of least resistance once it enters the bone—naturally along the cracks formed during the compression fracture. This further exacerbates the leakage.

The mixture also fills or substantially fills the cavity of the compression fracture and is limited to certain chemical composition, thereby limiting the amount of otherwise beneficial compounds that can be added to the fracture zone to improve healing. Further, a balloon must first be inserted in the compression fracture and the vertebra must be expanded before the cement is injected into the newly formed space.

A vertebroplasty device and method that eliminates or reduces the risks and complexity of the existing art is desired. A vertebroplasty device and method that is, not based on injecting a liquid directly into the compression fracture zone is desired.

BRIEF SUMMARY OF THE INVENTION

An expandable support device for performing completely implantable spinal repair is disclosed. The device may include a near end portion and a far end portion with a number of backbone struts extending therebetween. The near and far end portions may be closed or have passage openings. In one variation of the invention the end portions can be non-expandable and can cause the implant to form a tapered profile when expanded. Adjacent backbone struts in the implant can be connected by a number of deformable-support struts. The adjacent backbone struts can be affixed together or integral (e.g., when laser cut from a tube or other extrusion type piece).

The structure of the implant device can permit expansion a number of directions. Variations of the implant can assume different cross-sectional shapes, where such shapes include a square, rectangular, triangular, or any such type of polygon where the sides are defined by the adjacent backbone struts and associated connecting support struts. Furthermore, the shapes may also be rounded, tapered, rectangular (e.g., where the aspect ratio may not be 1 to 1.)

An expandable support device for placement within or between spinal vertebral bodies is disclosed. The device can have a radially non-expandable near end portion, a radially non-expandable far end portion and a longitudinal axis extending therebetween. The device can have backbone struts parallel to the longitudinal axis. The backbone struts can each have a near end integral with the near end portion and a far end integral with the far end portion. The device can have deformable support struts located between each adjacent backbone strut. The support struts can have a support strut width perpendicular to the longitudinal axis. The support struts can have a support strut thickness parallel to the longitudinal axis. The support strut width can be greater than the support strut thickness. Each support strut can be deformable such that, upon longitudinal expansion of the expandable support device from a radially expanded configuration, the adjacent backbone struts approach each other while the support struts deform. One or more of the support struts can have a bend when the device is in a radially contracted configuration. The bend can define an edge having a surface that is coincidental with the outer surface of the expandable support device. When the device is in a radially contracted configuration a first length of the backbone struts can be the same shape as the first length of the backbone struts when the device is in a radially expanded configuration. When the device is in a radially expanded configuration, the device can have a lumen along the longitudinal axis. The lumen can be at least partially filled with a filler. An outer cross section of the device perpendicular to the longitudinal axis when the device is in a radially expanded configuration can be quadrilateral. Lengths of at least two backbone struts can be parallel with each other when the device is in a radially expanded configuration.

An expandable support device for placement within or between spinal vertebral bodies is disclosed. The device can have a radially non-expandable near end portion, a radially non-expandable far end portion and a longitudinal axis extending therebetween. The device can have backbone struts parallel to the longitudinal axis. The backbone struts can each have a near end integral with the near end portion and a far end integral with the far end portion. The device can have deformable support struts located between each adjacent backbone strut. Each support strut can be deformable such that, upon longitudinal expansion of the expandable support device from a radially expanded configuration, the adjacent backbone struts approach each other while the support struts deform. When the device is in a radially expanded configuration, the device can have a lumen along the longitudinal axis. The lumen can be at least partially filled with a filler. An outer cross section of the device perpendicular to the longitudinal axis when the device is in a radially expanded configuration can be quadrilateral. At least one support strut can have a bend when the device is in a radially contracted configuration. The bend can defines an edge having a surface that is coincidental with the outer surface of the expandable support device.

An expandable support device for placement within or between spinal vertebral bodies is disclosed. The device can have a radially non-expandable near end portion, a radially non-expandable far end portion and a longitudinal axis extending therebetween. The device can have backbone struts parallel to the longitudinal axis. The backbone struts can each have a near end integral with the near end portion and a far end integral with the far end portion. The device can have deformable support struts located between each adjacent backbone strut. At least a first support strut and a second support strut located between an adjacent pair of backbone struts can be flat when the device is in a radially expanded configuration. Each support strut can be deformable such that, upon longitudinal expansion of the expandable support device from a radially expanded configuration, the adjacent backbone struts approach each other while the support struts deform. When the device is in a radially contracted configuration a first length of the backbone struts can be the same shape as the first length of the backbone struts when the device is in a radially expanded configuration. When the device is in a radially expandable configuration, the device can have a lumen along the longitudinal axis. The lumen can be at least partially filled with a filler. An outer cross section of the device perpendicular to the longitudinal axis when the device is in a radially expanded configuration can be quadrilateral. At least one support strut can have a bend when the device is in a radially contracted configuration. The bend can define an edge having a surface that is coincidental with the outer surface of the expandable support device. A flat plane can be defined by the outer surfaces of the support struts between a first backbone strut and a second backbone strut adjacent to the first backbone strut.

A method for repairing a damaged section of a spine is also disclosed. The method can include expanding an expandable support device in a treatment site such as a damaged section of bone (e.g., vertebra) or soft tissue (e.g., vertebral disc). The expandable support device can be loaded on a balloon during the expanding. The expansion of the device may be accomplished as described herein. For example, the expansion may include can include inflation of a balloon-type expansion device. Inflating the balloon can include inflating the balloon equal to or greater than about 5,000 kPa of internal pressure, or equal to or greater than about 10,000 kPa of internal pressure.

Expandable support devices for orthopedic applications, deployment tools and methods for using that same that can be deployed in a minimally invasive procedure are disclosed. For example, the expandable support devices can be deployed through 0.25 in. to 0.5 in. incisions. The expandable support devices can be, for example, metal and/or polymer self-assembling, self-forming structures. Imaging modalities can be used to maneuver the expandable support device inside the patient.

Further, expandable support devices, deployment tools and methods are disclosed for removing, resizing, and repositioning the expandable support devices are disclosed.

BRIEF DESCRIPTION OF THE DRAWINGS

FIG. 5 illustrates a side view of the variation of the implant of FIG. 1 in an expanded configuration.

FIG. 6 shows a variation of the view along line 6-6 in FIG. 4

FIGS. 9 through 11 illustrate a variation of a method for accessing a treatment site in the vertebra.

FIGS. 33 and 35 illustrate a variation of a method for splitting the expandable support device with an engagement device.

FIGS. 36a and 36b illustrate variations of a first portion and second portion, respectively, of the expandable support device that has been slit.

DETAILED DESCRIPTION

Figure 1:
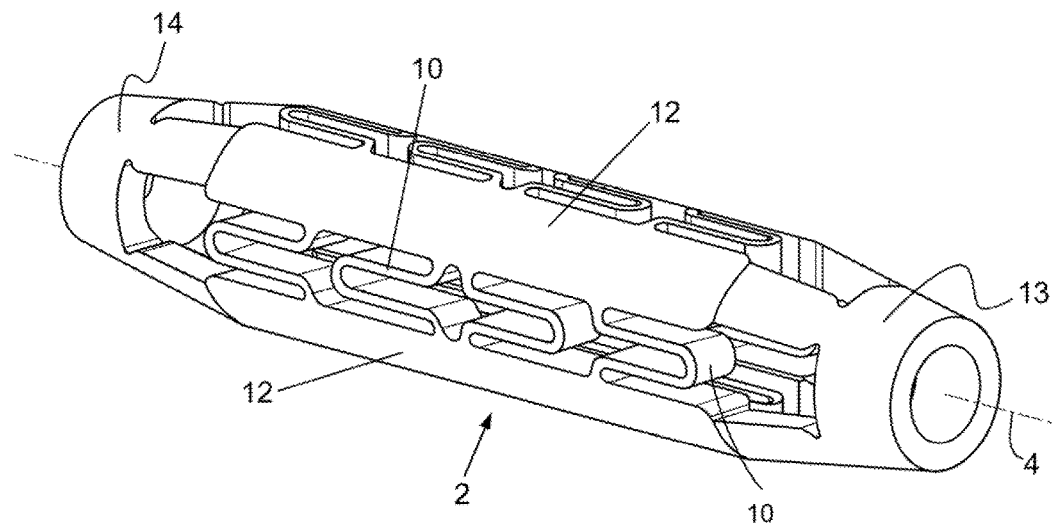
FIG. 1 illustrates a perspective view of a variation of the implant in an unexpanded configuration.
Figure 2:
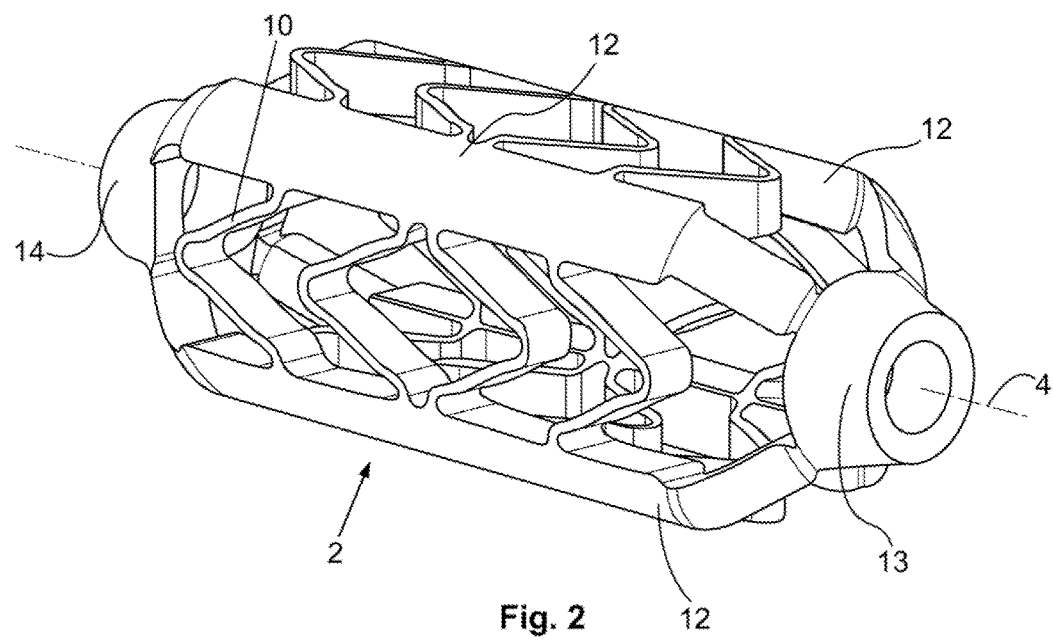
FIG. 2 illustrates a perspective view of the variation of the implant of FIG. 1 in an expanded configuration.

FIGS. 1 and 2 illustrate a biocompatible implant used for tissue repair, including, but not limited to repair of bone fractures such as spinal compression fractures, and/or repairing soft tissue damage, such as herniated/diseased vertebral discs. The implant can be used to perform vertebroplasty, and/or the implant can be used as a partial and/or complete vertebra and/or vertebral disc replacement, and/or for vertebral fixation. The implant can be an expandable support device 2, for example a stent. The expandable support device 2 can have a longitudinal axis 4.

The expandable support devices 2 can be used to provide structural reinforcement from inside one or more bones, as a replacement for one or more bones, or between bones. The expandable support devices can be used for a variety of orthopedic locations, such as in the vertebral column, for example, to treat compression fractures. Examples of expandable support devices and methods for use of expandable support devices, as well as devices for deploying the expandable support devices include those disclosed in the following applications which are all incorporated herein in their entireties: PCT Application Nos. US2005/034115, filed 21 Sep. 2005; US2005/034742, filed 26 Sep. 2005; US2005/034728, filed 26 Sep. 2005; US2005/037126, filed 12 Oct. 2005; U.S. Provisional Application Nos. 60/675,543, filed 27 Apr. 2005; 60/723,309, filed 4 Oct. 2005; 60/675,512, filed 27 Apr. 2005; 60/699,577, filed 14 Jul. 2005; 60/699,576, filed 14 Jul. 2005; and 60/752,183 filed 19 Dec. 2005.

The expandable support device 2 can have a plurality of backbone struts 12. The backbone struts 12 can connect a near end portion 13 and a far end portion 14. The backbone struts 12 can each have a near end and a far end affixed to the respective end portions 13 and 14. The expandable support device 2 can be constructed of separate structures that are fixed, integrated or otherwise joined together. The expandable support device 2 can be fabricated from a uniform stock of material (e.g., via laser cutting, or electrical discharge machining (EDM)). Adjacent backbone struts can be joined by a number of deformable support struts 10. The support struts 10 can have, a thinner cross sectional thickness than most of the remainder of the stent. This feature allows for pre-determined deformation of the stent 2 to take place.

The support struts 10 may also serve to distribute load across the backbone strut. In such cases, the number of support struts will determine the degree to which the backbone struts are supported.

The expansion ratio of the expandable support device 2 can be, for example, about 3 or about 4 times the initial diameter of the expandable support device 2. The expansion ratio can be selected as required for the particular procedure. For example, in the pre-expanded configuration the expandable support device 2 can have an initial diameter of about 6.3 mm (0.25 in.), while in the expanded configuration, the diameter can be about 9.5 mm, (0.37 in.). In a further example, the expandable support device 2 can have an initial diameter of about, 5 mm (0.2 in.), while in the expanded configuration, the diameter can be about 20 mm (0.8 in.).

In the pre-expanded configuration, the cross-sectional shape of the expandable support device 2 can be circular, triangular, oval, rectangular, square, or any type of polygon and/or rounded, and/or tapered shape. Upon expansion, the expandable support device 2 can form a polygon-type shape, or other shape as discussed herein.

FIG. 2 illustrates that the expandable support device 2 can expand such that the backbone struts 12 can expand away from the longitudinal axis 4. The backbone struts 12 can remain substantially parallel to the axis 4. The support struts 10 can be configured to limit the expansion of the backbone struts 12. The backbone struts 12 can be configured to prevent the backbone struts 12 from buckling.

The adjacent backbone struts 12 and accompanying support struts 10 can form a side of the implant. Although the variation illustrated in FIGS. 1 through 6 shows four backbone struts 12, and four support struts 10 per adjacent backbone struts 12 (and therefore four faces), the inventive device can have three or more sides, for example with the requisite number of backbone supports. The cross sectional areas of the expandable support device, can include triangular shapes, square shapes, rectangular shapes, and any type of polygon-shaped structure, for example when the expandable support device 2 is in an expanded configuration. The longitudinal length of each side of the expandable support device 2 can be equal to the other sides or sides of the expandable support device 2. The longitudinal length of each side of the expandable support device 2 can be substantially different than the other sides or sides of the expandable support device 2.

Any portion of the expandable support device 2 can have one or more ingrowth ports (not shown). The ingrowth ports can be configured to encourage biological tissue ingrowth therethrough during use. The ingrowth ports can be configured to releasably and/or fixedly attach to a deployment tool or other tool. The ingrowth ports can be configured to increase, and/or decrease, and/or focus pressure against the surrounding biological tissue during use. The ingrowth ports can be configured to increase and/or decrease the stiffness of either the backbone or support struts.

The expandable support device 2 can have any number of support struts 10. The support struts 10 can have a substantially "V"-like shape that deforms or expands as the implant expands, such as shown in FIG. 2. The shape of the support struts 10 can be shapes other than the substantially "V"-like shape. The struts 10 can be configured as any shape to accommodate the expansion of the implant 2. Such shapes can include a substantially "U"-like shape, a substantially "W"-like configuration, an substantially "S"-like configuration. The struts can have a combination of configurations in the same expandable support device 2, for example, to time the expansion of portions of the implant or otherwise control the profile of the implant during expansion.

The expandable support device 2 can have a wall thickness from about 0.25 mm (0.098 in.) to about 5 mm (0.2 in.), for example about 1 mm (0.04 in.). The expandable support device 2 can have an inner diameter (e.g., between farthest opposing backbone structures). The inner diameter can be from about 0.1 mm (0.04 in.) to about 30 mm (1.2 in.), for example about 6 mm (0.2 in.). The wall thickness and/or the inner diameter can vary with respect to the length along the longitudinal axis 4. The wall thickness and/or the inner diameter can vary with respect to the angle formed with a plane parallel to the longitudinal axis 4. The wall thickness can be reduced at points where deformation is desired. For example, the wall thickness of the support struts 10 can be reduced where the backbone structure meets the end portions.

Figure 3:
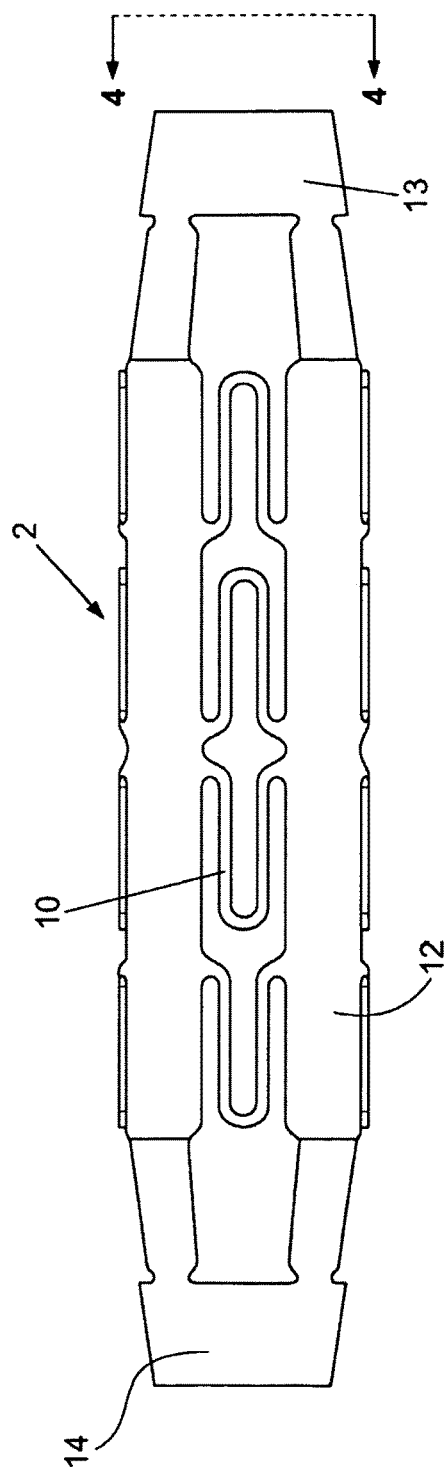
FIG. 3 illustrates a side view of the variation of the implant of FIG. 1.

FIG. 3 illustrates that the implant 2 can have near and far end portions 13 and 14. The near and far end portions 13 and 14 can be attached to each backbone strut via a near and far end of the backbone strut 12.

Figure 4:
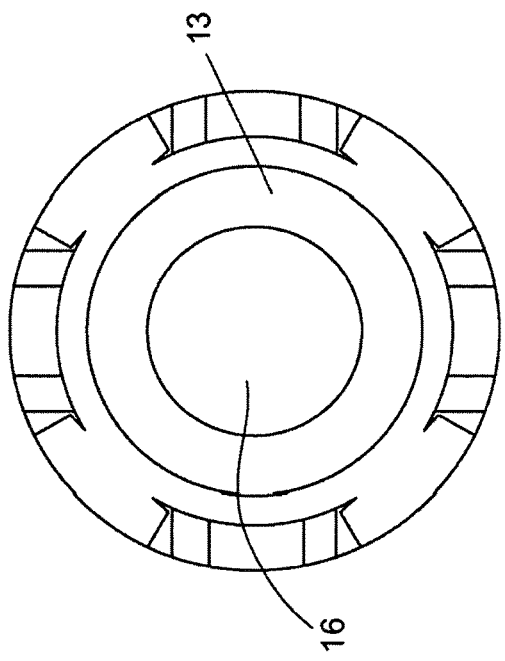
FIG. 4 shows a variation of the view along line 4-4 in FIG. 3.

FIG. 4 illustrates a front view of the implant 2 taken along the line 4-4 of FIG. 3. The end portions of the expandable support device 2 can have openings 16. The opening 16 can be threaded to accommodate a threaded member. One or both of the end portions can be solid which allows for filling of the expandable support device 2 with materials described herein. The end portions can be expandable. The end portions can be non-expandable (i.e., rigid).

FIG. 5 illustrates that after expansion the backbone struts 18 can remain parallel to the longitudinal axis 4 and the ends of the backbone struts can form a taper with the near and far end portions 13 and 14.

FIG. 6 illustrates a front view taken along the line 6-6 of FIG. 5 of the expandable support device 2. The expandable support device 2 can have a square cross sectional shape as the backbone struts 12 remain parallel to the longitudinal axis 4.

The expandable support device 2 can have one or more protrusions on the surface of the expandable support device 2. The protrusions can have features such as tissue hooks, and/or barbs, and/or cleats. The protrusions can be integral with and/or fixedly or removably attached to the expandable support device 2. The expandable support device 2 can be configured (e.g., on the support struts 10 or other parts of the implant) to burrow into soft bone (e.g., cancellous or diseased), for example, until the device fully expands, or until the device hits the harder vertebral endplates.

Any or all elements of the expandable support device 2 and/or other devices or apparatuses described herein (e.g., including all deployment tools and their elements described below) can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphthalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support device 2 and/or other devices or apparatuses described herein (e.g., including all deployment tools and their elements described below), can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The expandable support device 2 and/or elements of the expandable support device 2 and/or other devices or apparatuses described herein (e.g., including all deployment tools and their elements described below) and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co. Inc. Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Method of Use

Figure 7:
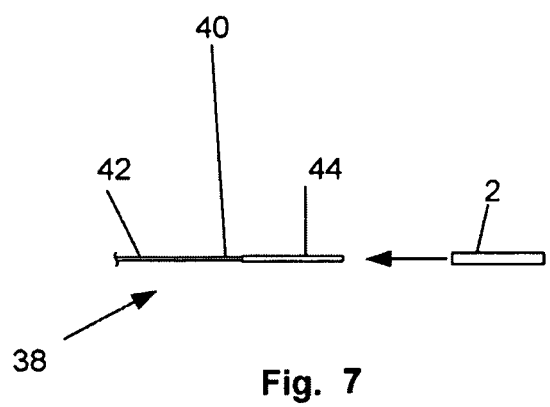
FIGS. 7 and 8 illustrate a variation of a method for using a delivery system for the expandable support element.

FIG. 7 illustrates that the expandable support device 2 can be loaded in a collapsed (i.e., contracted) configuration onto a deployment tool 38. The deployment tool 38 can have an expandable balloon catheter as known to those having an ordinary level of skill in the art. The deployment tool 38 can have a catheter 40. The catheter 40 can have a fluid conduit 42. The fluid conduit 42 can be in fluid communication with a balloon 44. The balloon 44 and the deployment tool 38 can be the balloon 44 and deployment tool 38 as described by PCT Application No. US2005/033965 filed 21 Sep. 2005, which is herein incorporated by reference in its entirety. The balloon 44 can be configured to receive a fluid pressure of at least about 5,000 kPa (50 atm), more narrowly at least about 10,000 kPa (100 atm), for example at least about 14,000 kPa (140 atm).

The expandable support device 2 can be deployed and/or expanded with a force from a mechanical actuation device (e.g., as opposed to the balloon expansion). For example, the ends of the expandable support device 2 can move, or be moved, together to expand the backbone struts outward. The expandable support device 2 can be configured to be self-expand upon the removal of a restraint (e.g., when the expandable support device 2 is constructed from a resilient or super-elastic material). The expandable support device 2 can be made from a shape memory alloy that can have a pre-determined transition temperature such that expansion takes place due to temperature changes passively (e.g., from the patient's body heat) or actively (e.g., from thermal and/or electrical energy delivered to the expandable support device 2 from outside the patient) created during or after implantation.

The expandable support device 2 can be locked into the expanded configured with a locking structure (e.g., a center strut, ratchet type mechanism, screw, locking arm, combinations thereof that can be integral with or separate from the remainder of the expandable support device 2. The expandable-support device 2 can be "locked" into the expanded position by filing the expandable support device 2 with cement, filler (bone chips, calcium sulfate, coralline hydroxyapatite, Biocoral tricalcium phosphate, calcium phosphate, PMMA, bone morphogenic proteins, other materials described herein, or combinations thereof.

The deployment tool 38 can be a pair of wedges, an expandable jack, other expansion tools, or combinations thereof.

Figure 8:
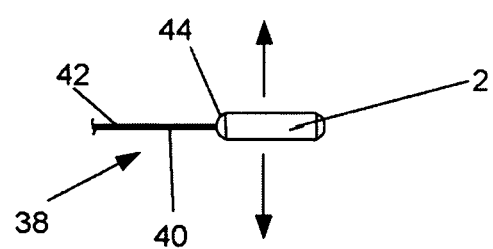

FIG. 8 illustrates that the fluid pressure in the fluid conduit 42 and balloon can increase, thereby inflating the balloon 44, as shown by arrows. The expandable support device 2 can expand, for example, due to pressure from the balloon 44.

FIGS. 9 (side view) and 10 (top view) illustrates a group of bones, such as vertebral column 46, that can have one or more bones, such as vertebra 48, separated from the other vertebra 48 by soft tissue, such as vertebral discs 50. The vertebra 48 can have a target or damage site 52, for example a compression fracture.

An access tool 54 can be used to gain access to the damage site 52 and or increase the size of the damage site 52 to allow deployment of the expandable support device 2. The access tool 54 can be a rotating or vibrating drill 56 that can have a handle 58. The drill 56 can be operating, as shown by arrows 60. The drill 56 can then be translated, as shown by arrow 62, toward and into the vertebra 48 so as to pass into the damage site 52.

FIG. 11 illustrates that the access tool 54 can be translated, as shown by arrow, to remove tissue at the damage site 52. The access tool 54 can create an access port 64 at the surface of the vertebra 48. The access port 64 can open to the damage site 52. The access tool 54 can then be removed from the vertebra 48.

Figure 12:
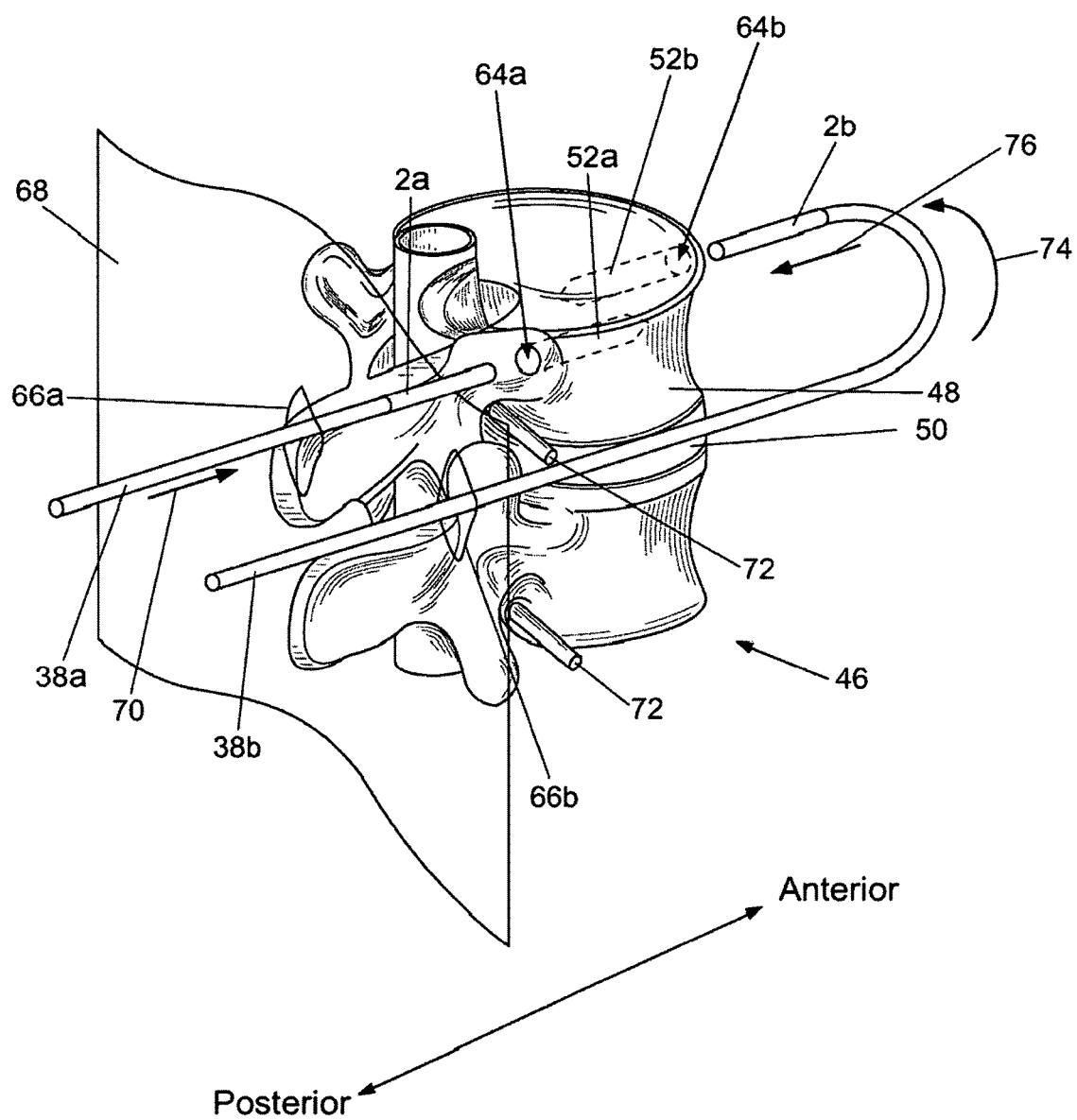
FIG. 12 illustrates various variations of methods for deploying the expandable support device to the vertebral column.

FIG. 12 illustrates that a first deployment tool 38a can enter through the subject's back. The first deployment tool 38a can enter through a first incision 66a in skin 68 on the posterior side of the subject near the vertebral column 46. The first deployment tool 38a can be translated, as shown by arrow 70, to position a first expandable support device 2a into a first damage site 52a. The first access port 64a can be on the posterior side of the vertebra 48.

A second deployment tool 38b can enter through a second incision 66b (as shown) in the skin 68 on the posterior or the first incision 66a. The second deployment tool 38b can be translated through muscle (not shown), around nerves 72, and anterior of the vertebral column 46. The second deployment tool 38b can be steerable. The second deployment tool 38b can be steered, as shown by arrow 74, to align the distal tip of the second expandable support device 2b with a second access port 64b on a second damage site 52b. The second access port 64b can face anteriorly. The second deployment tool 38b can translate, as shown by arrow 76, to position the second expandable support device 2 in the second damage site 52b.

The vertebra 48 can have multiple damage sites 52 and expandable support devices 2 deployed therein. The expandable support devices 2 can be deployed from the anterior, posterior, either or both lateral, superior, inferior, any angle, or combinations of the directions thereof.

Figure 13:
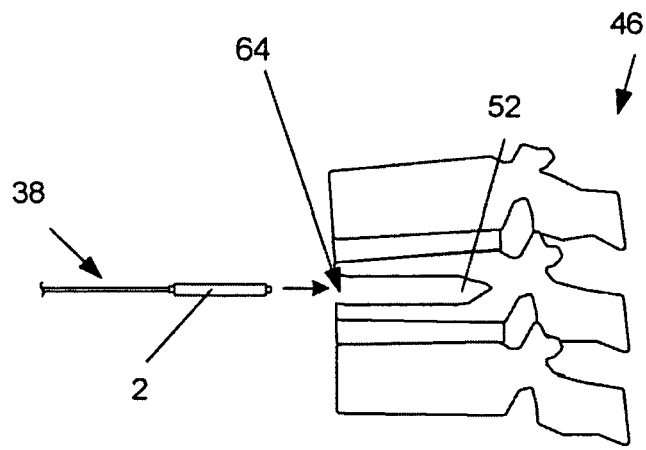
FIGS. 13 through 15 illustrate a variation of a method for deploying the expandable support device into the treatment site in the vertebra.
Figure 14:
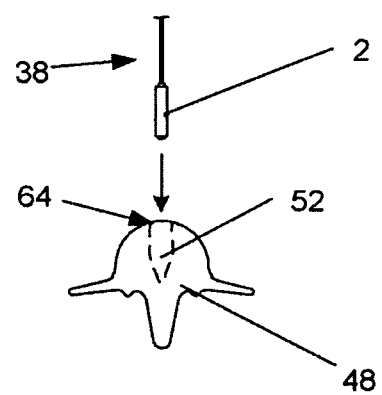
Figure 15:
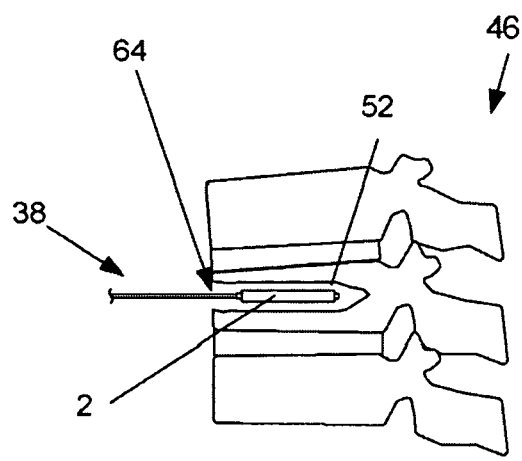

FIGS. 13 and 14 illustrate translating, as shown by arrow, the deployment tool 38 loaded with the expandable support device 2 through the access port 64. FIG. 15 illustrates locating the expandable support device 2 on the deployment tool 38 in the damage site 52.

Figure 16:
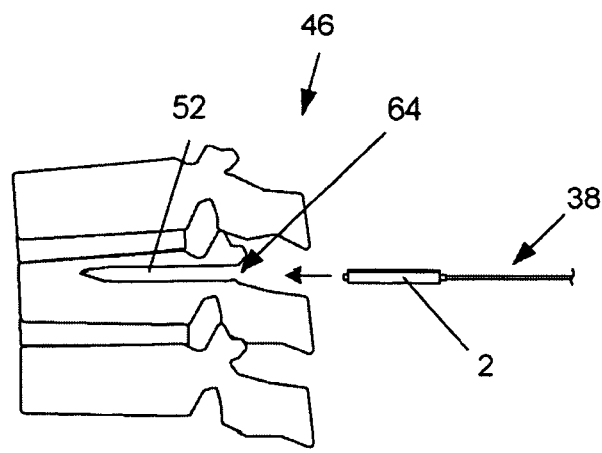
FIGS. 16 and 17 illustrate a variation of a method for deploying the expandable support device into the treatment site in the vertebra.
Figure 17:
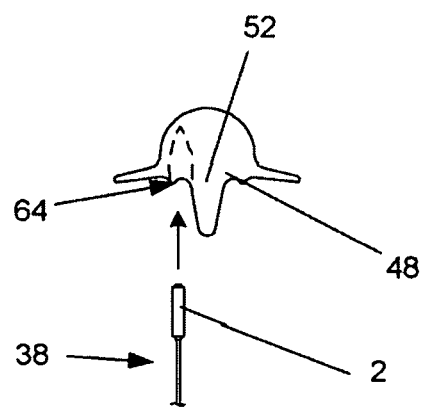

FIGS. 16 and 17 illustrate that the deployment tool 38 can be deployed from the posterior side of the vertebral column 46. The deployment tool 38 can be deployed off-center, for example, when approaching the posterior side of the vertebral column 46.

Figure 18:
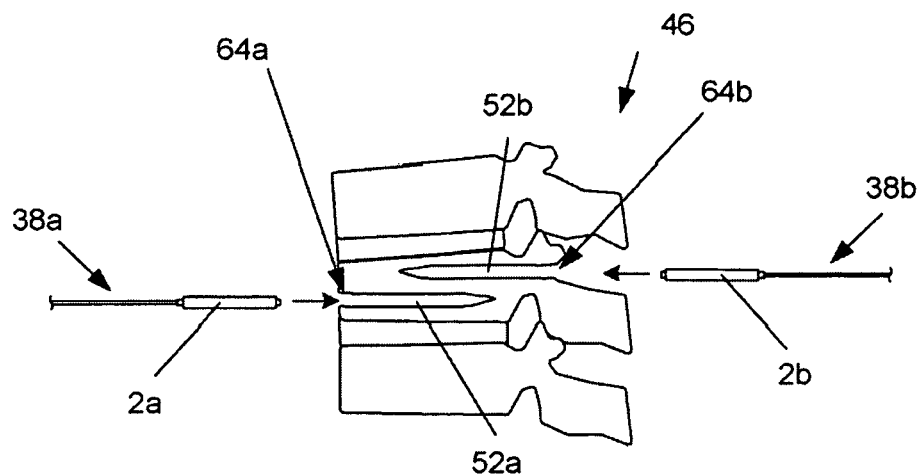
FIGS. 18 and 19 illustrate a variation of a method for deploying one or more expandable support devices into one or more treatment sites in the vertebra.
Figure 19:
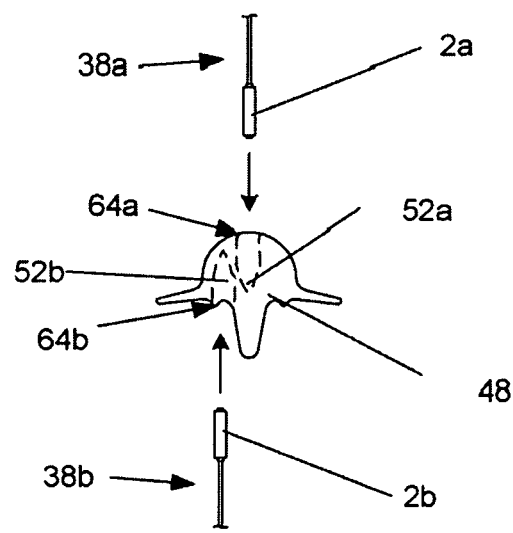

FIGS. 18 and 19 illustrate that first and second deployment tools 38a and 38b can position and deploy first and second expandable support devices 2a and 2b simultaneously, and/or in the same vertebra 48 and into the same or different damage sites 52a and 52b.

Figure 20:
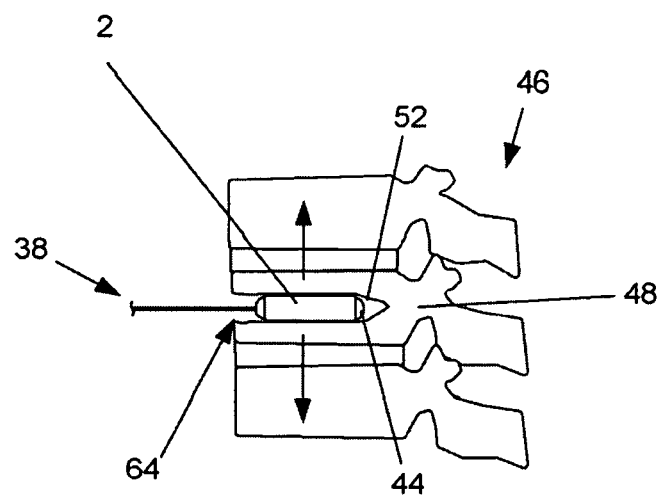
FIG. 20 illustrates a variation of a method for deploying the expandable support device into the treatment site in the vertebra.

FIG. 20 illustrates that the fluid pressure in the fluid conduit 42 and the balloon 44 can increase, thereby inflating the balloon 44, as shown by arrows. The expandable support device 2 can expand, for example, due to, pressure from the balloon 44. The balloon 44 can be expanded until the expandable support device 2 is substantially fixed to the vertebra 48. The balloon 44 and/or the expandable support device 2 can reshape the vertebral column 46 to a more natural configuration during expansion of the balloon 44.

Figure 21:
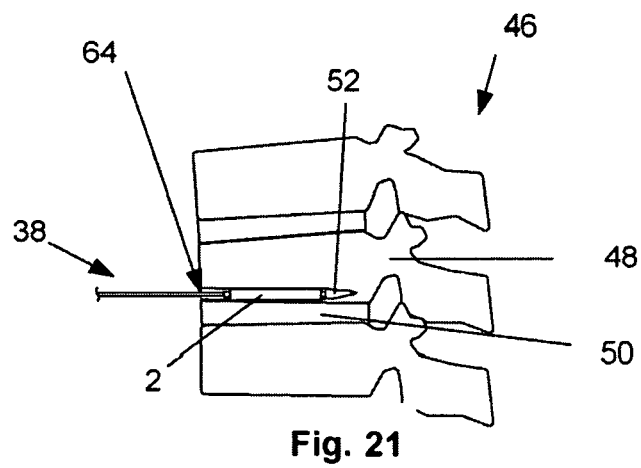
FIG. 21 illustrates a variation of a method for deploying the expandable support device into the treatment site in the vertebra.

FIG. 21 illustrates that the access port 64 can be made close to the disc 50, for example when the damage site 52 is close to the disc 50. The deployment tool 38 can be inserted through the access port 64 and the expandable support device 2 can be deployed as described supra.

Figure 22:
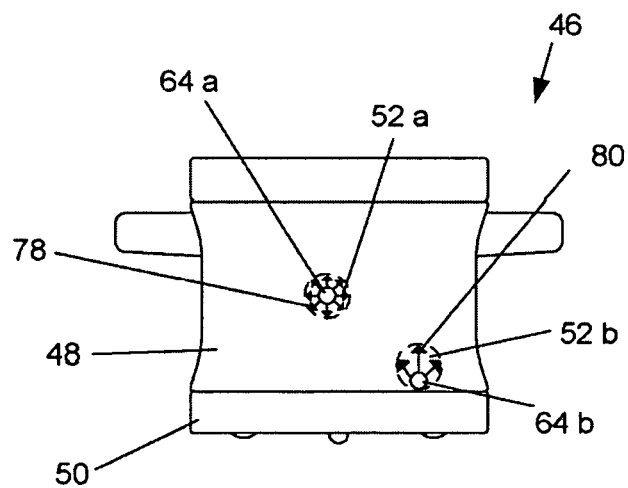
FIG. 22 illustrates a variation of a method for deploying multiple expandable 12 support devices into one or more treatment sites in the vertebra.

FIG. 22, a front view of the vertebral column, illustrates that more than one expandable support device 2 can be deployed into a single vertebra 48. For example, a first expandable support device (not shown) can be inserted through a first access port 64a and deployed in a first damage site 52a, and a second expandable support device (not shown) can be inserted through a first access port 64a and deployed in a second damage site 52b.

The first access port 64a can be substantially centered with respect to the first damage site 52a. The first expandable support device (not shown) can expand, as shown by arrows 78, substantially equidirectionally, aligned with the center of the first access port 64*a*. The second access port 64*b* can be substantially not centered with respect to the second damage site 52*b*. The second expandable support device (not shown) can substantially anchor to a side of the damage site 52 and/or the surface of the disc 50, and then expand, as shown by arrows 80, substantially directionally away from the disc 50.

Figure 23:
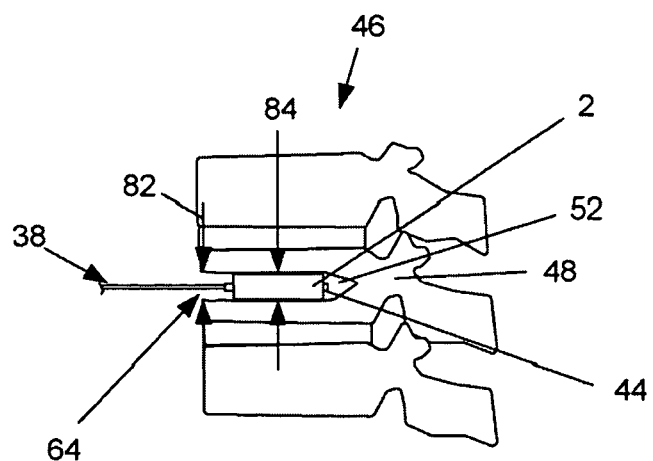
FIGS. 23 and 24 illustrate a variation of a method for deploying the expandable support device into the treatment site in the vertebra.

FIG. 23 illustrates that the fluid pressure can be released from the balloon 44, and the balloon 44 can retune to a pre-deployment configuration, leaving the expandable support element substantially fixed to the vertebra 48 at the damage site 52.

The access port 64 can have an access port diameter 82. The access port diameter 82 can be from about 1.5 mm (0.060 in.) to about 40 mm (2 in.), for example about 8 mm (0.3 in.). The access port diameter 82 can be a result of the size of the access tool 54. After the expandable support device 2 is deployed, the damage site 52 can have a deployed diameter 84. The deployed diameter 84 can be from about 1.5 mm (0.060 in.) to about 120 mm (4.7 in.), for example about 20 mm (0.8 in.). The deployed diameter 84 can be greater than, equal to, or less than the access port diameter 82.

Figure 24:
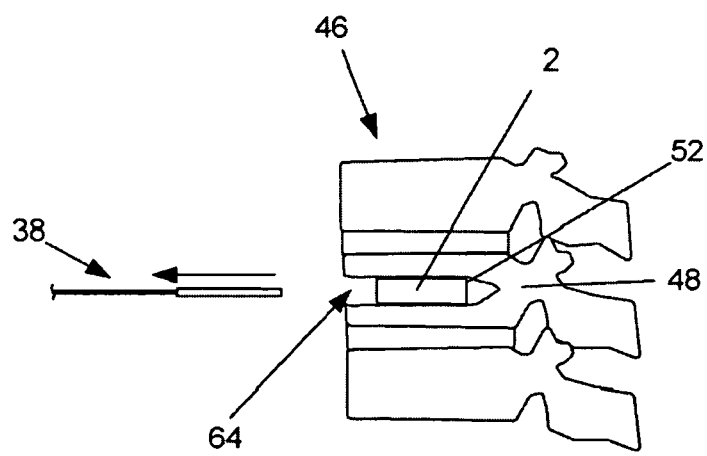

FIG. 24 illustrates that the deployment tool 38 can be removed, as shown by arrow, from the vertebra 48 after the expandable support device 2 is deployed.

Figure 25:
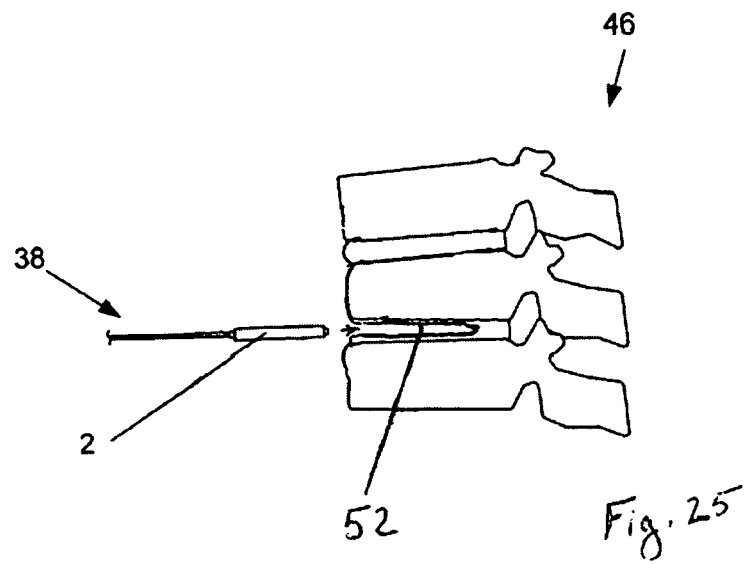
FIGS. 25 and 26 illustrate a variation of a method for deploying the expandable support device between vertebral bodies.
Figure 26:
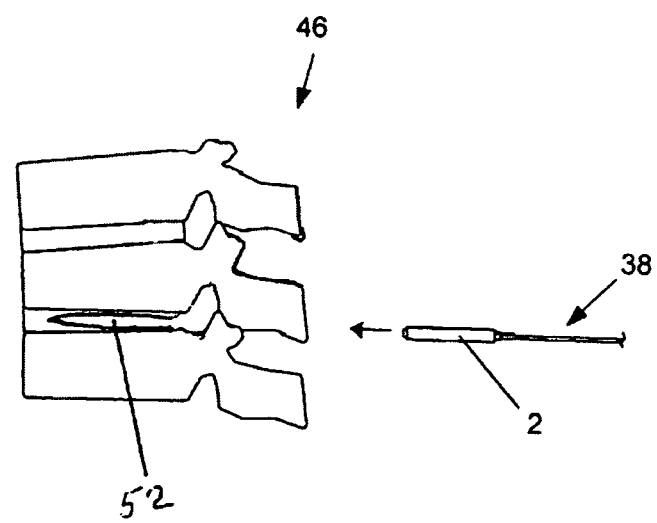

FIGS. 25 and 26 illustrate the expandable support device 2 can be placed between the vertebral bodies into a defect 52 of the vertebral disc. FIG. 25 illustrates an anterior approach to inserting the expandable support member between vertebral bodies. FIG. 26 illustrates a posterior approach to inserting the expandable support member. The expandable support member can also be inserted from a lateral approach.

The expandable support device 2 can be configured to create a cavity or otherwise displaces bone and/or tissue to form a space within the target sites during deployment (e.g., (luring radial expansion). For example, the struts of the expandable support device 2 can be configured so the radial expansion of the expandable support device 2 can move and/or compact bone/tissue. The struts can be configured to be narrow such that, on expansion, the struts move a relatively smaller amount of bone and/or tissue such that the struts do not compact the tissue.

After the expandable support device 2 has been initially deployed (i.e., inserted, and/or radially expanded) into the treatment site, the expandable support device 2 can be retracted, removed, resized, repositioned, and combinations thereof. The expandable support device 2 can be retracted and/or removed, and/or resized, and/or repositioned, for example, about 0 to about 2 months after initial deployment and/or the latest removal, and/or resizing, and/or repositioning.

Figure 27:
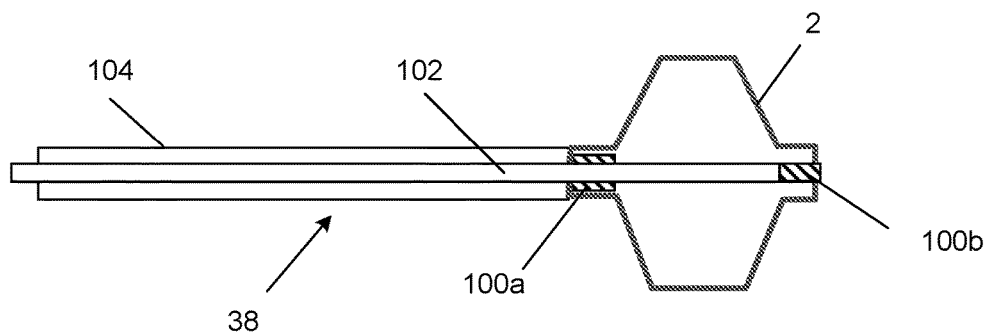
FIGS. 27 through 29 illustrate a variation of a method for adjusting and/or retracting the expandable support device with an engagement device.

FIG. 27 illustrates that the deployment tool 38, such as an engagement device, can be configured to attach to the implanted expandable support device. The engagement device can have one or more engagement elements 100, such as first and second engagement elements 100*a* and 100*b*. The engagement elements 100 can be on the radial inside and/or radial outside of the engagement device. For example, the engagement elements can be on an inner rod 102 that can be translatably and/or rotationally slidably attached to an outer handle 104. The engagement elements 106 can be a screw thread, a keyed slot, a toggle, ball and socket, an interference fit, a clip, a ratchet, a magnet, glue, an expanding anchor clip, an abutment, a hook, or combinations thereof. The engagement device can be the deployment device (e.g., the deployment tool or other device originally used to deploy the expandable support device 2).

FIG. 27 illustrates that the engagement device 38 can attach to the expandable support device 2. The expandable support device 2 can be configured to releasably attach to the engagement elements 100 at discrete locations (e.g., along discrete lengths of the inner diameter of the expandable support device 2).

The first engagement element 100*a* can attach to the proximal end of the expandable support device 2. The first engagement element 100*a* can be an abutment. The second engagement element 100*b* can attach to the distal end of the expandable support device 2. The second engagement element 100*b* can be a threaded outer surface. The expandable support device 2 can have a threaded inner radius, for example, that can be configured to engage the threaded outer surface of the second engagement element 100*b*.

Figure 28:
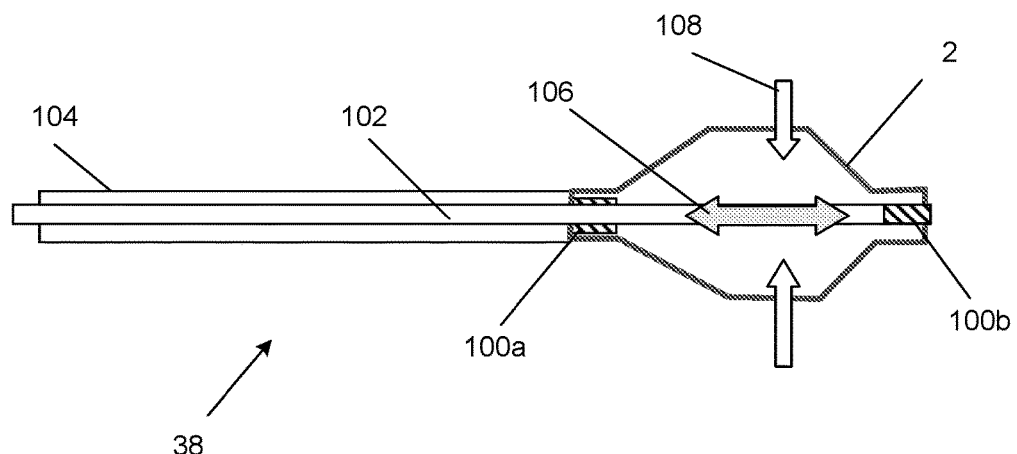

FIG. 28 illustrates that a tensile force, as shown by arrows 106, can be applied to the ends of the expandable support device 2, for example, via the engagement device 38 and the first and second engagement elements 100*a* and 100*b*. For example, the inner rod 102 can be pushed distally while the outer handle 104 can be concurrently pulled proximally. The radius of the expandable support device 2 can contract, as shown by arrows 108.

Figure 29:
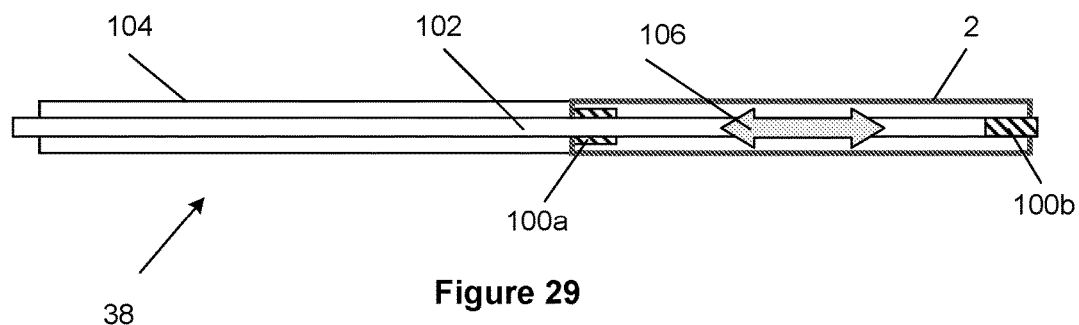

FIG. 29 illustrates that the tensile force, shown by arrows 106, can longitudinally expand the expandable support device. The expandable support device can radially contract, for example, until the expandable support device 2 is in a configuration completely or substantially equivalent to the configuration of the expandable support device 2 before the original deployment of the expandable support device to the treatment site. For example, the expandable support device 2 can have a maximum outer radius that is equal to or smaller than the inner radius of the portion (e.g., the outer handle 104) of the deployment tool 38 into which the expandable support device 2 can be configured to retract.

The expandable support device 2 can be withdrawn from the target site, and/or retracted into the engagement device 38.

Figure 30:
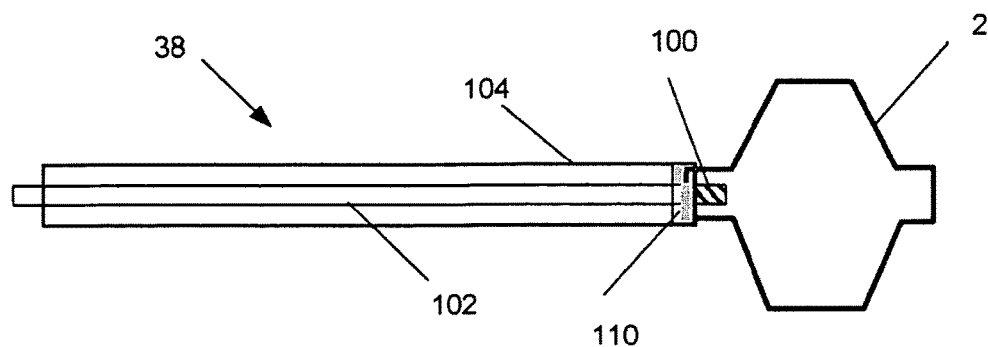
FIGS. 30 through 32 illustrate a variation of a method for adjusting and/or retracting the expandable support device, with an engagement device.

FIG. 30 illustrates that the outer handle 104 can be, a sheath and/or a sheath can be radially outside or inside of the outer handle 104. The sheath can have a sheath entry 110. The sheath entry 110 can be at the distal end of the sheath. The sheath entry 110 can have a hard material edge, and/or a slippery polymer edge, and/or a tapered edge, and/or an expanding slotted tube front edge, and/or a sacrificial (e.g., breakaway) edge.

Figure 31:
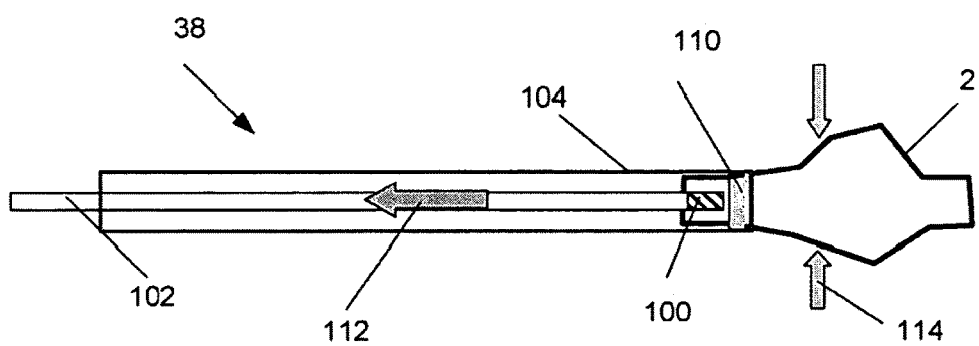

FIG. 31 illustrates that the sheath can be forced over the expandable support device 2, and/or the expandable support device 2 can be drawn, as shown by arrow 112, into the sheath.

FIG. 31 illustrates that the expandable support device 2 can radially contract, as shown by arrows 114, as the expandable support device 2 is completely or partially translated (e.g., withdrawn, retracted), as shown by arrow 112, into the sheath. The radial contraction of the expandable support device 2 can be resilient or forced deformation.

Figure 32:
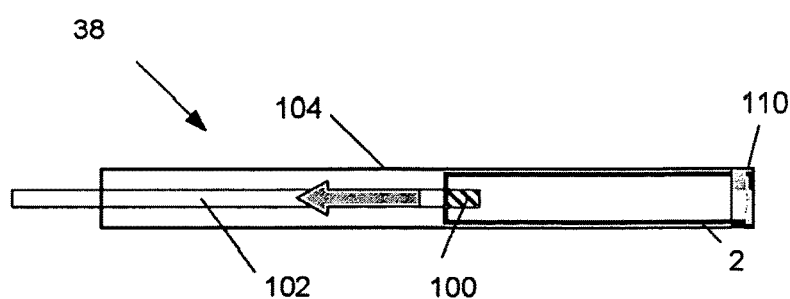

FIG. 32 illustrates that the expandable support device 2 can be completely withdrawn or retracted into the sheath. In a radially contracted configuration, the outer radius of the expandable support device 2 can be about equal to and/or smaller than the inner radius of the sheath. The deployment tool 38 and expandable support device 2 can be removed from the target site.

Figure 33:
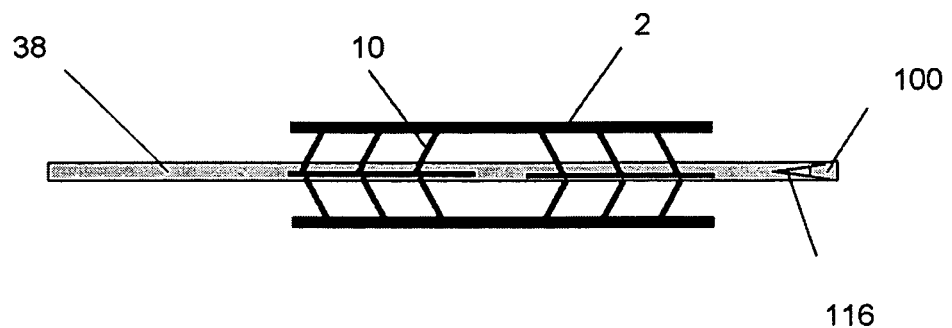

FIG. 33 illustrates a side view of the engagement device 38 deployed through the expandable support device 2. The engagement device 38 can be deployed extending through the expandable support device 2, for example through a center channel or port.

Figure 34:
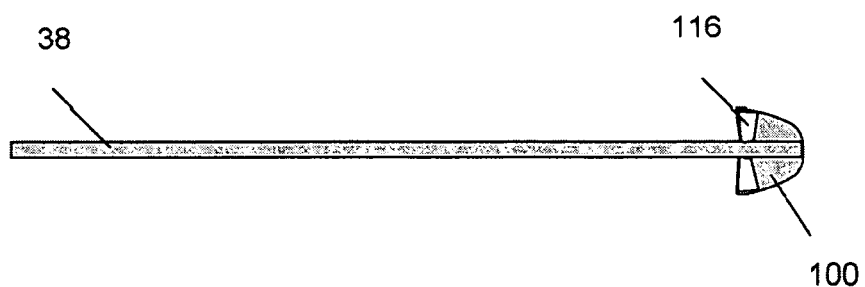
FIG. 34 illustrates a variation of the engagement device having a cutting blade.

FIG. 34 illustrates that the engagement device 38 can have an engagement element 100 that can be configured to unbuckle, tear, split, destroy, separate, cut, break or combinations thereof, the struts 10. The engagement element 100 can be a cutter saw 116, and/or otherwise have a bladed or sharp proximal side.

FIG. 35 illustrates that the engagement device 38 can be longitudinally translated, as shown by arrow, for example, drawing the engagement element 100 through the struts 10. The engagement element 100 can unbuckle, tear, split, destroy, separate, cut, break or combinations thereof, the struts 10. The engagement element 100 can partially or completely collapse or buckle the expandable support device 2, for example within the target or treatment site (e.g., bone cavity).

FIGS. 36*a* and 36*b* illustrate that the expandable support device 2 can be separated into two or more expandable support device pieces 118. The expandable support device pieces 118 can be removed and/or repositioned and/or resized individually and/or together from the target site.

Figure 37:
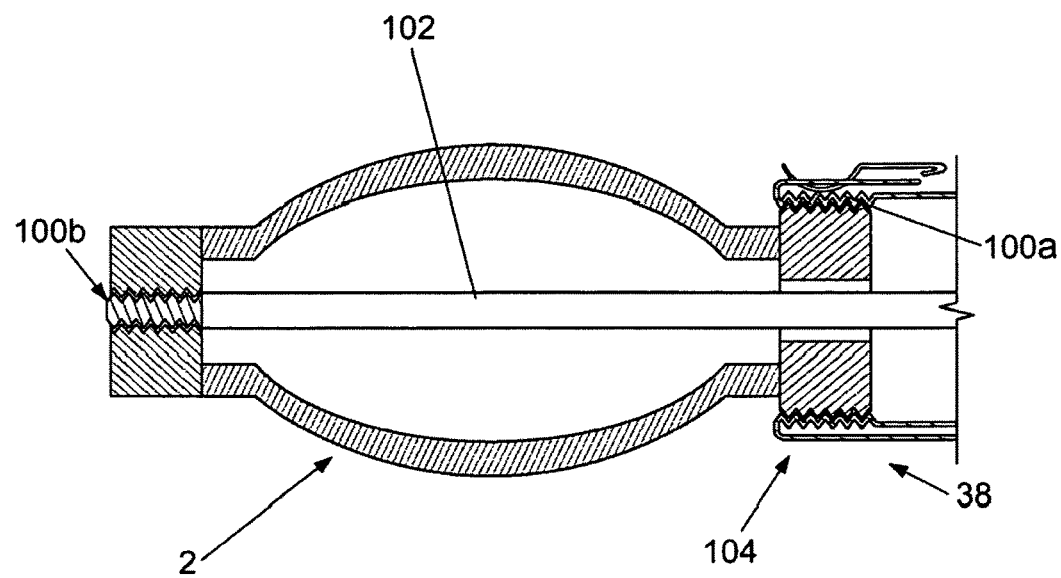
FIG. 37 illustrates a variation of a method for adjusting and/or retracting the expandable support device.

FIG. 37 illustrates a cross-sectional view of a method of adjusting the expandable support device similar to the method illustrated in FIGS. 27 through 29. The first engagement element 100*a* can be threading on the radial inside of the outer handle. The first engagement element 100*a* can be forced toward the second engagement element 100*b* (e.g., by pushing the outer handle 104 distally and pulling the inner rod 102 proximally), for example to radially expand and longitudinally contract the expandable support device 2. The first engagement element 100*a* can be forced away from the second engagement element 100*b* (e.g., by pulling the outer handle 104 proximally and pushing the inner rod 102 distally), for example to radially contract and longitudinally expand the expandable support device 2

The deployment tool 38 can be rotatably attached to and detached from the expandable support device 2. The outer handle 104 can contact the expandable support device 2 by completely encircling the first engagement element 100*a*, and/or by discretely contacting the first engagement element 100*a*, for example with a set of individual radially translatable arms that can be detached from the first engagement element 100*a* by translating the arms radially outward (or inward if necessary) from the first engagement element 100*a*.

The outer handle 104 and inner rod 102 can be detached and/or reattached in any combination to the expandable support device 2. For example, the expandable support device 2 can be positioned in the target site. The expandable support device 2 can then be radially expanded (e.g., by applying a longitudinally compressive force). The inner rod 102 can then be detached from the expandable support device 2. The expandable support device 2 can be repositioned by manipulating the expandable support device 2 with the outer handle 104. The outer handle 104 can then be detached from the expandable support device 2 and the deployment tool can be withdrawn from the target site and/or the inner rod 102 can be reattached to the expandable support device 2 and the expandable support device can be radially expanded, and/or radially contracted, and/or repositioned within the target site, and/or removed from the target site.

Figure 38:
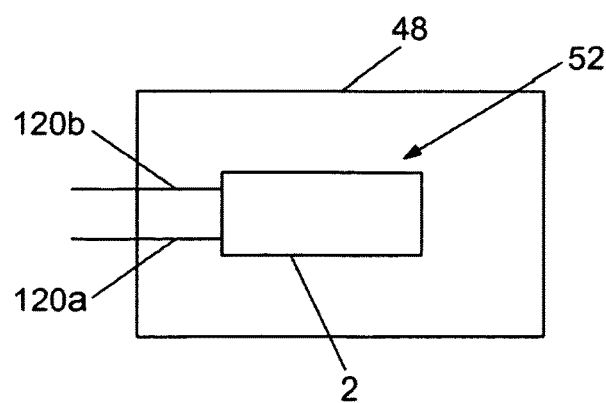
FIG. 38 illustrates a cross-sectional view of a method for deploying the expandable support device in a bone.

FIG. 38 illustrates a cross section of the expandable support device 2 implanted at a treatment site 52 in a bone 48. The expandable support device 2 can have one or more markers, such as a first marker 120*a* and/or a second marker 120*b*, attach to and/or be integral with the expandable support device 2. Any number of markers 120 can extend out of the bone 52. The markers 120 can be radiopaque, and/or echogenic. The markers 120 can be used, for example, to locate the expandable support device 2 (e.g., once the bone 48 has regrown around the treatment site 52).

The expandable support device 2 can, be configured to radially contract when a rotational (e.g., twisting) force is applied to the expandable support device 2. The expandable support device 2 can have a completely or partially coiled or otherwise spiral configuration. The expandable support device 2 can have a radius or height reduction based on a twisting effect.

The expandable support device 2 can be configured to be overdeployable. When the expandable support device 2 is overdeployed, the expandable support device 2 can return to a substantially pre-deployment configuration (e.g., having a pre-deployment radius, but in a different configuration otherwise).

Figure 39:
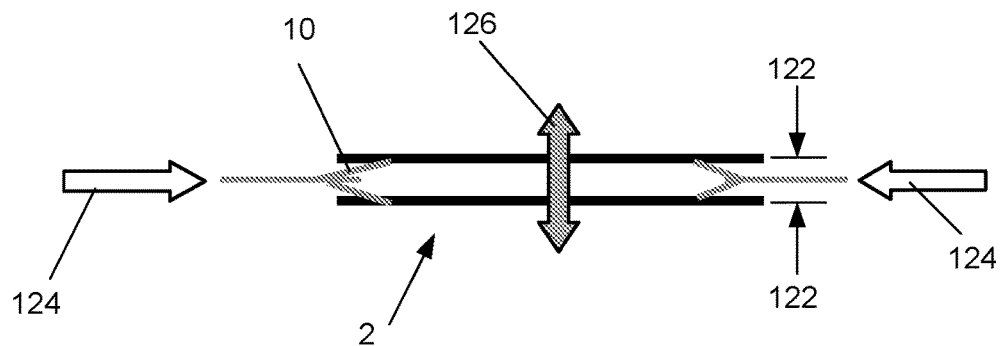
FIGS. 39 through 41 illustrate a variation of a method for overdeploying the expandable support device.
Figure 40:
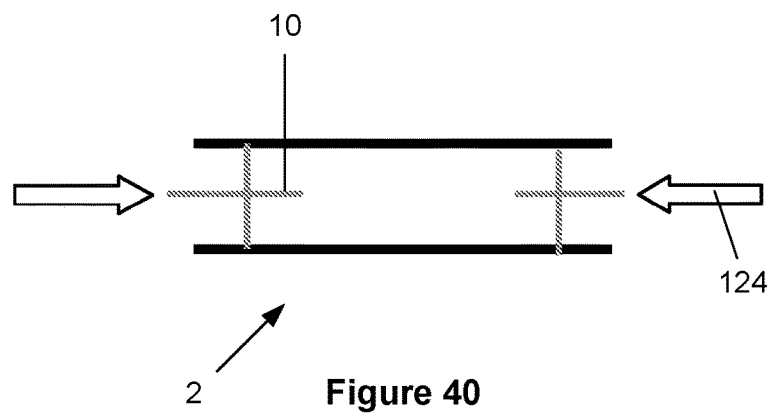
Figure 41:
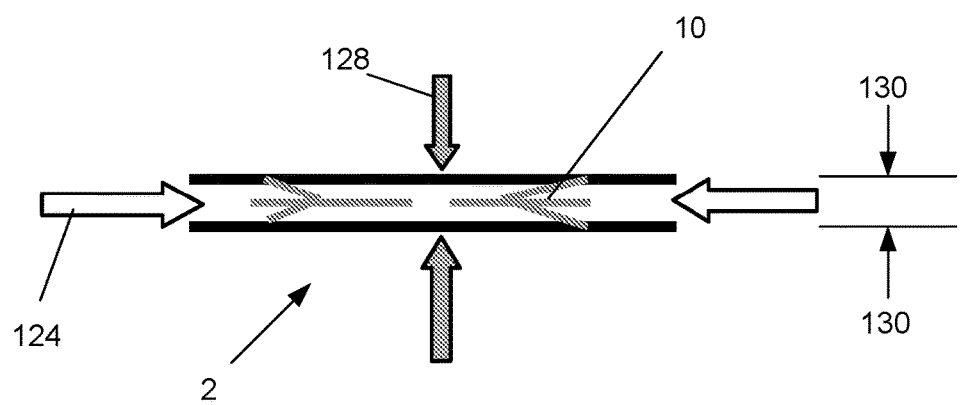

FIGS. 39 through 41 illustrate that the configuration of the struts 10 can cause the expandable support device 2 to have an overdeployment radius substantially equivalent to a pre-deployment radius 122. FIG. 39 illustrates the expandable support device 2 in a pre-deployment configuration. A longitudinally compressive force, as shown by arrows 124, can be applied. Radial expansion, as shown by arrows 126, can begin, for example due to the longitudinally compressive force.

FIG. 40 illustrates that when the expandable support device 2 is fully deployed, the expandable support device 2 has no radial expansion. The longitudinally compressive forces, as shown by arrows 124, can begin to force the struts longitudinally inward, for example beyond a configuration at the maximum radial expansion of the expandable support device 2. This overdeployment can cause a decrease in the radius of the expandable support device 2.

FIG. 41 illustrates that when the expandable support device 2 is overdeployed, the expandable support device 2 can radially contract, as shown by arrows 128. The expandable support device 2 can have an overdeployment radius 130 substantially equivalent to, or less than, or greater than the pre-deployment radius 122.

Figure 42:
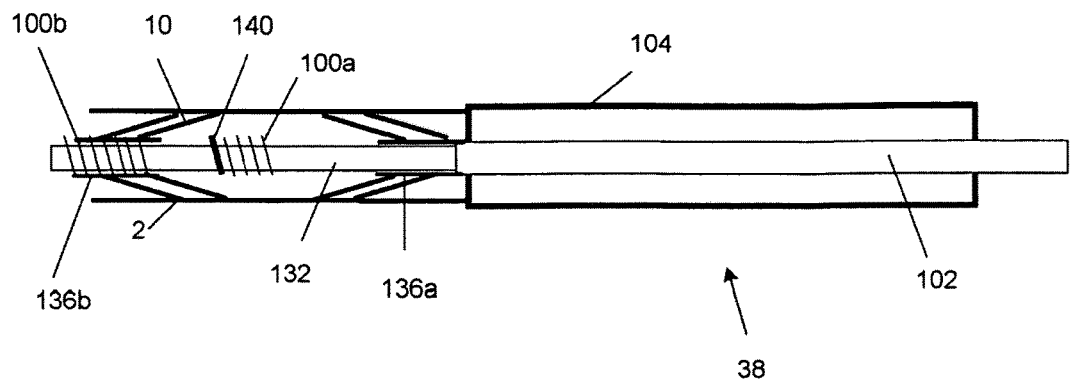
FIGS. 42 through 46 illustrate a method for deploying the expandable support device.

FIG. 42 illustrates that the expandable support device 2 can have a control element, such as internal control shaft 132. The internal control shaft 132 can be removably attached to the inner rod 102. The remainder of the expandable support element 2 can be removably and/or rotatably attached to the internal control shaft 132.

The internal control shaft 132 can have the first and second engagement elements 100*a* and 100*b*. The expandable support element 2 can have discrete first and second receivers 136*a* and 136*b* configured to removably attach to the first and second engagement elements 100*a* and 100*b*, respectively. For example, the first and second receivers 136*a* and 136*b* can be threaded.

The first engagement element 100*a* can have a stop or brake thread 140, for example configured to interference fit the first receiver 136*a*.

In an undeployed or pre-deployed (e.g., radially contracted) configuration, the second engagement element 100*b* can be attached to the second receiver 136*b*. The first engagement element 100*a* can be unattached to the first receiver 136*a*.

Figure 43:
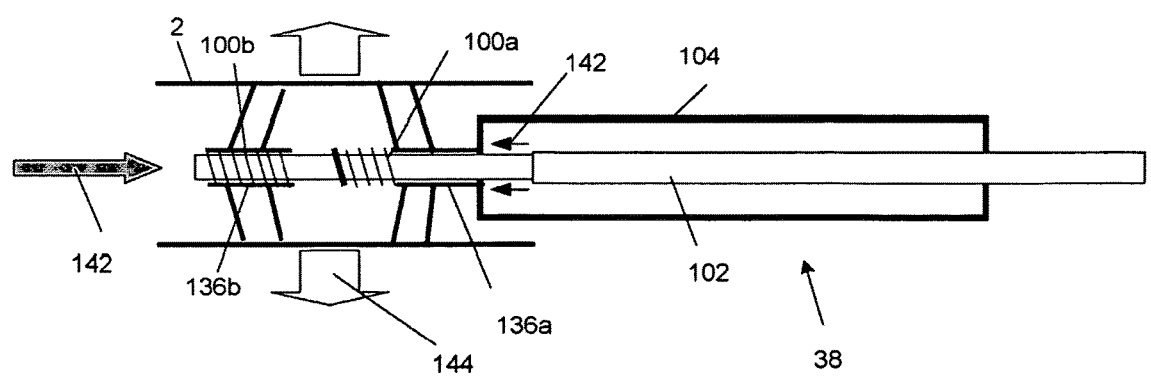

FIG. 43 illustrates that a compression force, shown by arrows 142, can be applied to the expandable support device 2. For example, the sliding rod 102 can be pulled proximally and the outside handle 104 can be pushed distally. The expandable support device 2 can be attached to the sliding rod 102 via the second engagement element 100b and the second receiver 136b. The expandable support device 2 can be attached to the outside handle 104 via abutting or otherwise engaging at the first receiver 136a or other element. The compression force can produce radial expansion, as shown by arrows 144, in the expandable support device 2.

Figure 44:
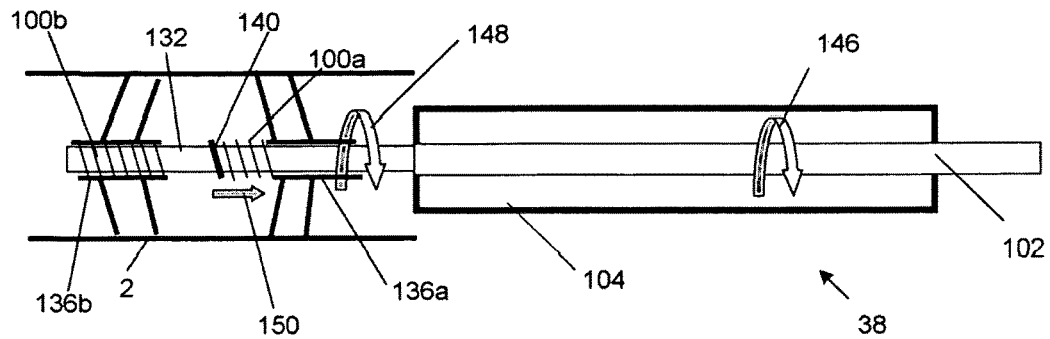

FIG. 44 illustrates that once the expandable support device 2 is substantially radial expanded, the inner rod can be rotated, as shown by arrow 146, with respect to the expandable support device 2 with the exception of the inner control shaft 148. (The expandable support device can be held rotationally stationary by the target site and/or by engagement between the outside handle and the expandable support device 2. The inner control shaft 132 can rotate as shown by arrow 148. The rotation of the second engagement element 100b wraith respect to the second receiver 136b can force the control shaft 132 to translate, as shown by arrow 150, with respect to the expandable support device 2. The expandable support device 2 can radially expand during the translation shown by the arrow 150.

Figure 45:
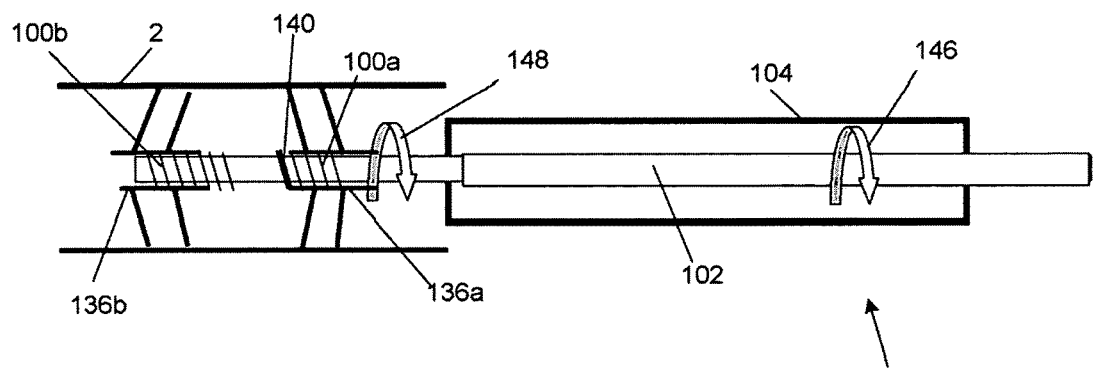

FIG. 45 illustrates that during the translation shown by arrow 150 in FIG. 44, the first engagement element 100a can engage the first receiver 136a. The second engagement element 100b can remain engaged to the second receiver 136b. The inner rod 102, control shaft 132, and first engagement element 136a can rotate with respect to the remainder of the expandable support device 2, for example until a safety element, such as the brake thread 140, stops the rotation. The brake thread 140 can interference fit with the first receiver 136a. The brake thread 140 can provide sufficient resistance to friction fit with the first receiver 136a. The safety element (e.g., stop or brake thread) can be on the first and/or second engagement elements 100a and/or 100b and/or first and/or second receivers 136a and/or 136b.

Figure 46:
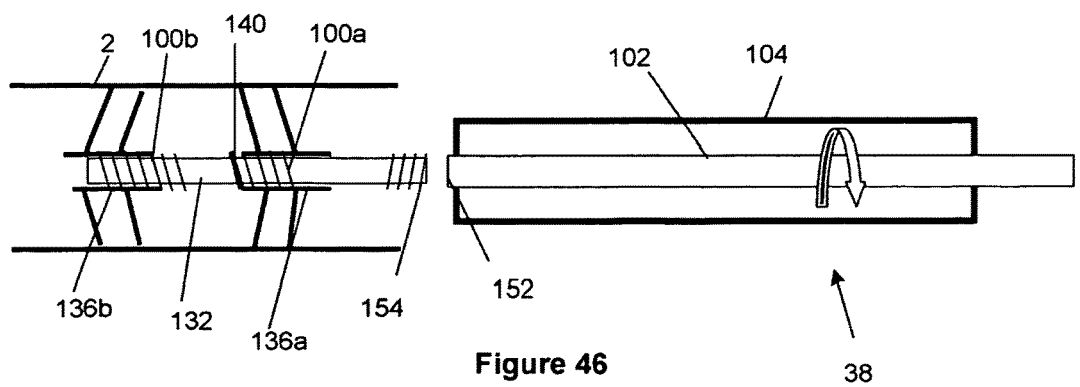

FIG. 46 illustrates that the inner control shaft 132 can be detached from the inner rod 102, for example at a coupling point 152. The coupling point 152 can include one or more detachable attachment elements, such as hooks, pegs and holes, thread knots and holes, radially translatable arms, teeth, threads, or combinations thereof. The inner control shaft 132 can have corresponding detachable attachment elements, such as threads 154. The threads can be in the same direction (e.g., with higher coefficients of friction) as the threads of the first and second engagement elements 100a and 100b, or counter-threaded with respect to the threads of the first and second engagement elements 100a and 100b. The coupling point 152 can be detached by deactivating or otherwise detaching the detachable attachment elements. For example, the inner rod 102 can be rotated or counter rotated as necessary, as shown by arrow. The inner control shaft 132 can remain rotationally fixed because, for example, the target site has substantially fixed the expandable support device and the brake thread 140 can fix the inner control shaft 132 to the expandable support device 2.

The deployment tool 38 can be removed from the target site. The expandable support device 2 can remain in the target site, for example, fixed in the deployed configuration (e.g., unable to substantially radially or longitudinally expand or contract) and/or bolstered by the inner control shaft 132. The deployment tool 38 can re-engage the expandable support device 2 and the above steps can be reversed to radially contract and retract, reposition, and/or remove the expandable support device 2 in or from the target site.

The expandable support device 2 can have a mechanical key or locking bar that can fix the expandable support device 2 in an expanded or otherwise deployed configuration. When the key or locking bar is removed from the expandable support device 2, the expandable support device 2 can be repositioned, and/or removed and/or resized (e.g., deconstructed), for example, automatically, resiliently radially compressed.

The expandable support device can be subject to fatigue, for example, to increase material brittleness resulting in fracture. The fractured pieces of the expandable support device can be removed, for example, by suction and irrigation. The engagement element can be a small grabber or gripper. The engagement element can induce oscillating motion in the struts. The oscillating motion can cause strut fatigue and failure, for example in the struts and/or in the joints. The oscillating motion can be ultrasonic, mechanical, hydraulic, pneumatic, or combinations thereof.

The expandable support device 2 can have receiving elements to engage the engagement elements. For example, the receiving elements can be hooks, barbs, threads, flanges, wedge shaped slots, dovetails, hinges, key holes, or combinations thereof.

The expandable support device 2 can have a leader. The leader can be a heavy wire. The leader can guide the engagement device into and/or over the implant. The engagement device 38 can radially contract the implant, for example, using a method described herein. The engagement device 38 and/or another tool can drill or otherwise destroy bone and/or other tissue to access the expandable support device 2.

The tissue surrounding the expandable support device 2 can be destroyed (e.g., chemically and/or electrically and/or thermally, such as by cauterization or electro-cauterization). The expandable support device 2 can be removed and/or repositioned and/or resized once the surrounding tissue is completely or substantially destroyed.

The expandable support device 2 can be mechanically destroyed. For example, the expandable support device can be mechanically compressed, for example by applying external radially and/or axially (i.e., longitudinally) contracting jaws. A snipper and/or microgrinder and/or saw can mechanical destroy the expandable support device.

The expandable support device 2 can be chemically destroyed using RF energy. For example UV energy can be delivered to dissolve a plastic expandable support device.

The expandable support device 2 can be biodegradable. The expandable support device 2 can be made from biodegradable materials known to those having ordinary skill in the art. The expandable support device 2 can be made from a magnesium based alloy that can degrade or a biodegrading polymer for example, PGA, PLA, PLLA, PCL.

The expandable support device 2 can be configured to device designed to dissolve when exposed to selected materials (e.g., in solution). For example, acetone can be applied to the expandable support device (e.g., made from PMMA). The surrounding tissues can be protected and/or the expandable support device can be fluidly contained before the dissolving solution is applied.

The expandable support device 2 can be dissolved, for example, by exposing the expandable support device to an electrolyte and electricity.

Imaging methods can be used in combination with the methods for deploying the expandable support device described herein. For example, imaging methods can be used to guide the expandable support device during deployment. The expandable support device 2 can have imaging markers (e.g., echogenic, radiopaque), for example to signal the three-dimensional orientation and location of the expandable support device during use of an imaging modality. Imaging modalities include ultrasound, magnetic resonance imaging (MRI, fMRI), computer tomography (CT scans) and computed axial tomography (CAT scans), radiographs (x-rays), fluoroscopy, diffuse optical tomography, elastography, electrical impedance tomography, optoacoustic imaging, positron emission tomography, and combinations thereof.

It is apparent to one skilled in the art that various changes and modifications can be made to this disclosure, and equivalents employed, without departing from the spirit and scope of the invention. Elements expressed herein as singular or plural can be used in the alternative (i.e., singular as plural and plural as singular). Elements shown with any embodiment are exemplary for the specific embodiment and can be used in combination on or with other embodiments within this disclosure.

We claim:

1. An expandable support device for placement within or between spinal vertebral bodies, comprising:
   a radially non-expandable near end portion, a radially non-expandable far end portion and a longitudinal axis extending therebetween;
   backbone struts parallel to the longitudinal axis, the backbone struts each having a near end integral with the near end portion and a far end integral with the far end portion;
   deformable support struts located between each adjacent backbone strut, wherein the support struts have a support strut width perpendicular to the longitudinal axis, and wherein the support struts have a support strut thickness parallel to the longitudinal axis, and wherein the support strut width is greater than the support strut thickness; and
   where each support strut is deformable such that, upon longitudinal expansion of the expandable support device from a radially expanded configuration, the adjacent backbone struts approach each other while the support struts deform;
   wherein a support strut comprises a bend when the device is in a radially contracted configuration, and wherein the bend defines an edge having a surface that is coincidental with the outer surface of the expandable support device;
   wherein when the device is in a radially contracted configuration a first length of the backbone struts is the same shape as the first length of the backbone struts when the device is in a radially expanded configuration;
   wherein when the device is in a radially expanded configuration, the device has a lumen along the longitudinal axis, and wherein the lumen is at least partially filled with a filler;
   wherein an outer cross section of the device perpendicular to the longitudinal axis when the device is in a radially expanded configuration is quadrilateral; and
   wherein lengths of at least two backbone struts are parallel with each other when the device is in a radially expanded configuration.

2. The device of claim 1, wherein upon radial expansion of the device the near end and far ends of the backbone struts do not expand as much as the remainder of the backbone strut such that they form a taper while the remainder of the backbone strut remain parallel to the longitudinal axis.

3. The device of claim 1, wherein the near end portion comprises an opening, wherein the opening in the near end comprises a threaded portion for receipt of a threaded member.

4. The device of claim 1, wherein the far end portion comprises an opening.

5. The device of claim 1, further comprising at least two support struts per adjacent backbone struts.

6. The device of claim 1, further comprising at least three backbone struts forming at least three sides of the implant.

7. The device of claim 1, where a cross sectional wall thickness of each support strut is less than a cross sectional wall thickness of the backbone strut so that the support strut deforms at a lower expansive force than the backbone strut.

8. The device of claim 1, wherein when the expandable support device is in the radially expanded configuration, the cross section of the expandable support device comprises a shape selected from the group consisting of a triangle, a rectangle, a square, and a polygon.

9. The device of claim 1, wherein the near end portion is tapered along the dimension of the longitudinal axis.

10. The device of claim 9, wherein the far end portion is tapered along the dimension of the longitudinal axis.

11. The device of claim 1, wherein the far end portion is tapered along the dimension of the longitudinal axis.

12. An expandable support device for placement within or between spinal vertebral bodies, comprising:
    a radially non-expandable near end portion, a radially non-expandable far end portion and a longitudinal axis extending therebetween;
    backbone struts parallel to the longitudinal axis, the backbone struts each having a near end integral with the near end portion and a far end integral with the far end portion;
    deformable support struts located between each adjacent backbone strut; and
    where each support strut is deformable such that, upon longitudinal expansion of the expandable support device from a radially expanded configuration, the adjacent backbone struts approach each other while the support struts deform; and
    wherein when the device is in a radially expanded configuration, the device has a lumen along the longitudinal axis, and wherein the lumen is at least partially filled with a filler; and
    wherein an outer cross section of the device perpendicular to the longitudinal axis when the device is in a radially expanded configuration is quadrilateral, and
    wherein at least one support strut comprises a bend when the device is in a radially contracted configuration, and wherein the bend defines an edge having a surface that is coincidental with the outer surface of the expandable support device.

13. The device of claim 12, wherein the near end portion is tapered along the dimension of the longitudinal axis.

14. The device of claim 13, wherein the far end portion is tapered along the dimension of the longitudinal axis.

15. The device of claim 12, wherein the far end portion is tapered along the dimension of the longitudinal axis.

16. An expandable support device for placement within or between spinal vertebral bodies, comprising:
    a radially non-expandable near end portion, a radially non-expandable far end portion and a longitudinal axis extending therebetween;

backbone struts parallel to the longitudinal axis, the backbone struts each having a near end integral with the near end portion and a far end integral with the far end portion;

deformable support struts located between each adjacent backbone strut, wherein at least a first support strut and a second support strut located between an adjacent pair of backbone struts are flat when the device is in a radially expanded configuration; and where each support strut is deformable such that, upon longitudinal expansion of the expandable support device from a radially expanded configuration, the adjacent backbone struts approach each other while the support struts deform;

wherein when the device is in a radially contracted configuration a first length of the backbone struts is the same shape as the first length of the backbone struts when the device is in a radially expanded configuration;

wherein when the device is in a radially expandable configuration, the device has a lumen along the longitudinal axis, and wherein the lumen is at least partially filled with a filler;

wherein an outer cross section of the device perpendicular to the longitudinal axis when the device is in a radially expanded configuration is quadrilateral;

wherein at least one support strut comprises a bend when the device is in a radially contracted configuration, and wherein the bend defines an edge having a surface that is coincidental with the outer surface of the expandable support device; and wherein a flat plane is defined by the outer surfaces of the support struts between a first backbone strut and a second backbone strut adjacent to the first backbone strut.

17. The device of claim 16, wherein the near end portion is tapered along the dimension of the longitudinal axis.

18. The device of claim 17, wherein the far end portion is tapered along the dimension of the longitudinal axis.

19. The device of claim 16, wherein the far end portion is tapered along the dimension of the longitudinal axis.

20. The device of claim 1, wherein the device has a wall thickness of 1 mm to 5 mm.

21. The device of claim 12, wherein the device has a wall thickness of 1 mm to 5 mm.

22. The device of claim 16, wherein the device has a wall thickness of 1 mm to 5 mm.

* * * * *